(12) United States Patent
Engbersen et al.

(10) Patent No.: US 9,012,424 B2
(45) Date of Patent: Apr. 21, 2015

(54) NANOGELS

(75) Inventors: Johannes Franciscus Joseph Engbersen, Hengelo (NL); Arkadi Vladimirovich Zinchenko, Moscow (RU)

(73) Assignee: 20MED Therapeutics B.V., Hengelo (NL)

( * ) Notice: Subject to any disclaimer, the term of this patent is extended or adjusted under 35 U.S.C. 154(b) by 0 days.

(21) Appl. No.: 14/122,668

(22) PCT Filed: May 25, 2012

(86) PCT No.: PCT/NL2012/050374
§ 371 (c)(1),
(2), (4) Date: Jan. 30, 2014

(87) PCT Pub. No.: WO2012/165953
PCT Pub. Date: Dec. 6, 2012

(65) Prior Publication Data
US 2014/0135376 A1   May 15, 2014

Related U.S. Application Data

(60) Provisional application No. 61/490,674, filed on May 27, 2011.

(30) Foreign Application Priority Data

May 27, 2011   (EP) .................................. 11167885

(51) Int. Cl.
*A61K 48/00* (2006.01)
*A61K 47/34* (2006.01)
*A61K 31/713* (2006.01)
*A61K 9/06* (2006.01)

(52) U.S. Cl.
CPC ............... *A61K 47/34* (2013.01); *A61K 31/713* (2013.01); *A61K 9/06* (2013.01); *Y10S 977/773* (2013.01); *Y10S 977/728* (2013.01)

(58) Field of Classification Search
USPC ..................... 424/486, 487; 514/44 R, 772.3; 525/451; 528/329.1, 332, 363, 367, 528/392; 977/773, 728
See application file for complete search history.

(56) References Cited

U.S. PATENT DOCUMENTS

| | | |
|---|---|---|
| 6,998,115 B2 | 2/2006 | Langer et al. |
| 7,427,394 B2 | 9/2008 | Anderson et al. |
| 2005/0244504 A1 | 11/2005 | Little et al. |
| 2008/0242626 A1 | 10/2008 | Zugates et al. |
| 2010/0028445 A1 | 2/2010 | Garnett et al. |
| 2010/0036084 A1 | 2/2010 | Langer et al. |
| 2010/0041739 A1 | 2/2010 | Lagunavicius et al. |

FOREIGN PATENT DOCUMENTS

WO   WO 2010/065660 A2   6/2010

OTHER PUBLICATIONS

International Search Report mailed Jul. 16, 2012 in International Appln. No. PCT/NL2012/050374.
Lin, Chao et al, "Novel Bioreducible Poly(amido amine)s for highly Efficient Gene Delivery," Bioconjugate Chemistry, vol. 18, No. 1, 2007, pp. 138-145.
Namgung, Ran et al., "Dual Bio-responsive Gene Delivery via Reducible Poly(amido amine) and Survivin-inducible Plasmid DNA," Biotechnology Letters, vol. 32, No. 6, Feb. 13, 2010, pp. 755-764.

(Continued)

*Primary Examiner* — Robert Jones, Jr.
(74) *Attorney, Agent, or Firm* — Gilberto M. Villacorta; Sunit Talapatra; Foley & Lardner LLP

(57) ABSTRACT

The present invention relates to a polymer according to Formulas (1) or (2): The present invention further relates to nanogels and nanoparticles made of a polymer according to general Formulas (1) and (2). The nanogels may comprise a biologically active component such as siRNA, miRNA, DNA, an (oligo)peptide or a proteins.

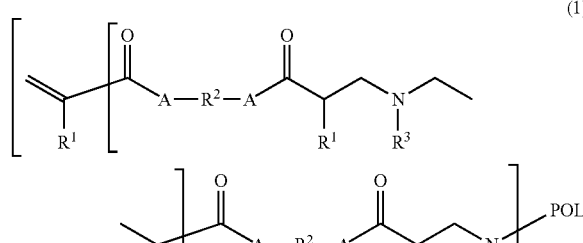

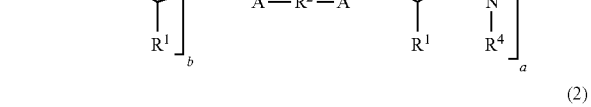

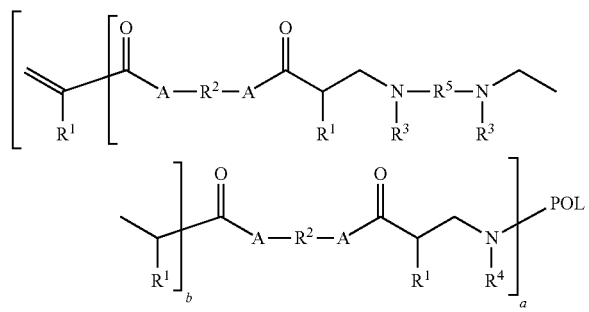

18 Claims, 11 Drawing Sheets

(56) References Cited

OTHER PUBLICATIONS

Vader, Pieter et al., "Disulfide-Based Poly(amido amine)s for siRNA Delivery: Effects of Structure on siRNA Complexation, Cellular Uptake, Gene Silencing and Toxicity," Pharmaceutical Research, vol. 28, No. 5, 2011, pp. 1013-1022.

Van Der Aa, L et al., "Poly(amido amine) Copolymers Derived from Aminobutanol and Ethylene Diamine are Excellent Carriers for siRNA Delivery," Journal of Controlled Release, vol. 148, 2010 pp. e85-e101 (abstract only).

Vercauteren, Dries et al., "Flotillin-dependent Endocytosis and a Phagocytosis-like Mechanism for Cellular Internalization of Disulfide-based Poly(amido amine)/DNA Polyplexes," Biomaterials, vol. 32, No. 11, Jan. 22, 2011, pp. 3072-3084.

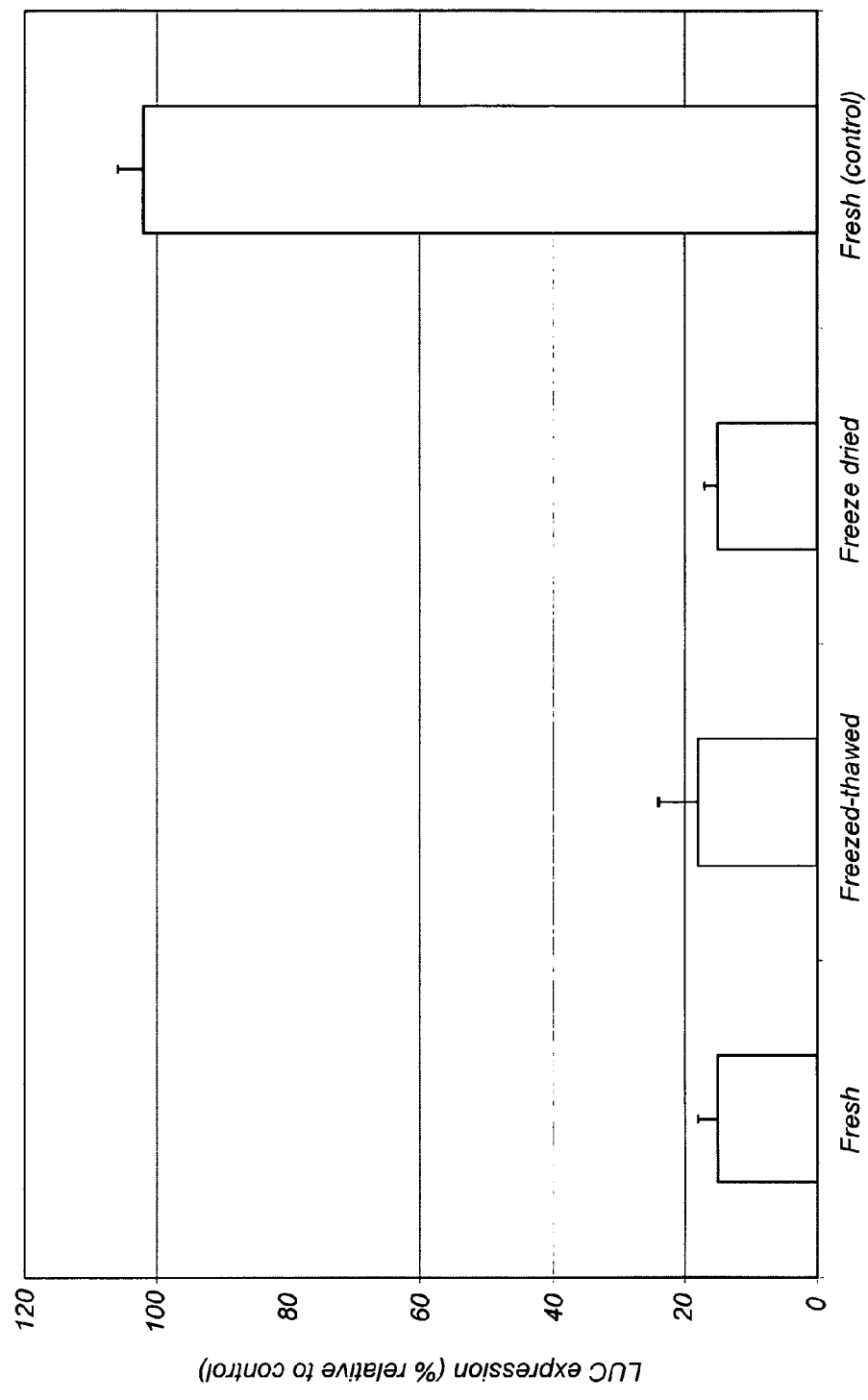

NANOGELS

CROSS-REFERENCE TO RELATED APPLICATIONS

This application is the National Phase of International Patent Application No. PCT/NL2012/050374, filed May 25, 2012, published as WO 2012/165953, which claims priority to European Application No. 11167885.0 and U.S. Provisional Application No. 61/490,674, both filed May 27, 2011. The contents of these applications are herein incorporated by reference in their entirety.

FIELD OF THE INVENTION

The present invention relates to the design and preparation of polymeric hybrid core-shell nanocarriers of which the core is designed to bind therapeutic payload (preferably therapeutic nucleotides, peptides, proteins, and small molecule drugs) and the shell is designed to protect the therapeutic payload, stabilize the nanocarrier, provide biocompatibility to the system, enable targeting to specific cells and tissue, and promote efficient intracellular release of the therapeutic payload from the nanocarrier.

More in particular, the present invention relates to PA polymers, nanoparticles and nanogels prepared from said PA polymers, wherein said nanogels may comprise a biologically active component selected from the group of RNA (in particular siRNAs or miRNAs) or derivatives or fragments hereof, DNA or derivatives or fragments hereof, (oligo)peptides and derivatives thereof, and proteins and derivatives thereof.

BACKGROUND OF THE INVENTION

The present invention is in the field of siRNA delivery (siRNA means Small Interfering RNA which is also known as Short Interfering RNA or Silencing RNA) and miRNA delivery (miRNA means Micro RNA).

RNA interference (RNAi) represents a promising strategy to affect the expression of disease-causing genes due to its ability to silence gene expression in a sequence-specific manner. Screening of different siRNA sequences resulted in the identification of several potential therapeutic oligonucleotides for different therapeutic applications. Nevertheless, the delivery of siRNA is a major problem. Naked siRNA is rapidly degraded by nucleases in biological fluid (the half life is in the order of minutes), and generally a carrier is required that provides sufficient protection against degradation in the extracellular environment and ensures efficient crossing of cellular barriers during intracellular uptake and processing. In particular, the highly negative charged siRNA can pass cell membranes only with great difficulty. Moreover, once in the intracellulair fluid, efficient unpacking of siRNA from the carrier is required to display its therapeutic activity. As a consequence, various non-viral, polymeric carriers for efficient delivery of RNA, DNA and siRNA have been investigated.

US 2002/0131951 (now U.S. Pat. No. 6,998,115), US 2004/0071654 (now U.S. Pat. No. 7,427,394), US 2005/0244504 and US 2010/0036084, all incorporated by reference, disclose poly(amino ester) polymers prepared from bisacrylamides and functionalized primary amines. In their cationic form, the poly(amino ester) polymers form complexes with DNA molecules or fragments thereof.

US 2008/0242626, incorporated by reference, discloses poly(amino ester) polymers based on bisacrylamides and functionalized primary amines, wherein the poly(amino ester) polymers are subjected to an end-modification. Wherein the poly(amino ester) polymer is amino-substituted, the poly(amino ester) polymer is reacted with an electrophile. Wherein the poly(amino ester) polymer is acrylate-substituted, the poly(amino ester) polymer is reacted with a nucleophile. These end-modified poly(amino ester) polymers are used for the delivery of DNA and RNA.

WO 2010/065660, incorporated by reference, discloses biodegradable polydisulfide amines and complexes thereof with e.g. RNA, DNA, siRNa and other oligonucleotides.

US 2010/0041739, incorporated by reference, discloses polyalkylene imine polymers which can be used for the delivery of e.g. DNA.

US 2010/0028445, incorporated by reference, discloses poly(amido amine) polymers comprising pendant disulfide groups, pendant thiol groups or pendant activated thiol groups and a method for preparing such poly(amino amine) polymers, wherein bisacryloyl monomers are reacted with a primary amine and/or a secondary diamine wherein one of the amines contains a disulfide group. The poly(amino amine) polymers can be converted into hydrogels by forming disulfide groups between poly(amino amine) chains.

C. Lin et al., Bioconjug. Chem. 18, 138-145, 2007, incorporated by reference, discloses poly(amido amine)s containing disulfide linkages which are prepared by a Michael addition of primary amines and disulfide-containing N,N'-cystamine bisacrylamide.

L. J. van der Aa et al., J. Control. Release 148, e85, 2010, incorporated by reference, disclose poly(amido amine)s containing disulfide linkages which are prepared by a Michael addition of primary aminoalcohols, disulfide-containing N,N'-cystamine bisacrylamide and 1,2-diaminoethane.

R. Namgung et al., Biotechnol. Lett. 32, 755, 2010, incorporated by reference, discloses poly(amido amine)s containing disulfide linkages which are prepared by a Michael addition of 4-amino-1-butanol and disulfide-containing N,N'-cystamine bisacrylamide.

P. vader et al., Pharm. Res. 28, 1013, 2011, incorporated by reference, discloses poly(amido amine)s containing disulfide linkages which are prepared by a Michael addition of 4-amino-1-butanol, disulfide-containing N,N'-cystamine bisacrylamide and 1,2-diaminoethane.

D. Vercauteren et al., Biomaterials 32, 3072, 2011, incorporated by reference, discloses poly(amido amine)s containing disulfide linkages which are prepared by a Michael addition of 4-amino-1-butanol and disulfide-containing N,N'-cystamine bisacrylamide.

The cationic polymeric systems known from the prior art have still several disadvantages. In particular, the need for the presence of excess of (cytotoxic) polymer in the therapeutic formulation, the frequently low handling and storage stability of the therapeutically loaded nanogels, as well as limited efficiencies in endosomal escape and cytosolic unpacking of the therapeutic payload (nucleotide) from the complex are still major challenges in this field.

SUMMARY OF THE INVENTION

The present invention relates to a PA (PolyAcryl) polymer according to the general Formulas (1) and (2):

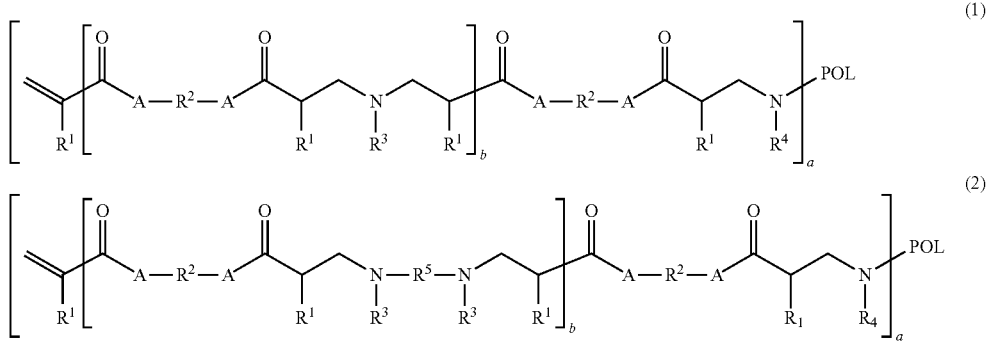

wherein:

A is independently selected from a direct carbon-carbon single bond (i.e. a structure wherein A is absent), O, $N(R^1)$ and S;

$R^1$ is independently selected from H and $CH_3$;

$R^2$ is independently selected from the group consisting of:
(a) $C_1$-$C_{40}$ alkylene, wherein the alkylene group may be linear or branched and is optionally substituted and/or is optionally (partly) unsaturated and/or is optionally interrupted by one or more heteroatoms, wherein the heteroatoms are independently selected from O, N and S, and/or wherein the alkylene group is interrupted by one or more —S—S— groups;
(b) $C_3$-$C_{40}$ cycloalkylene, wherein the cycloalkylene group is optionally substituted and/or is optionally (partly) unsaturated and/or optionally comprises one or more heteroatoms in the ring, wherein the heteroatoms are independently selected from O, N and S, and/or wherein the cycloalkylene group is interrupted by one or more —S—S— groups outside the ring;
(c) $C_6$-$C_{40}$ arylene, wherein the arylene group is optionally substituted;
(d) $C_6$-$C_{40}$ heteroarylene, wherein the heteroarylene group comprises one, two or three heteroatoms independently selected from O, N and S and/or wherein the heteroarylene group is optionally substituted;
(e) $C_7$-$C_{40}$ alkylarylene wherein the alkylarylene group is optionally substituted and/or wherein an alkyl part of the alkylarylene group is linear or branched and is optionally (partly) unsaturated and/or is optionally interrupted by one or more heteroatoms, wherein the heteroatoms are independently selected from O, N and S, and/or wherein an alkyl part of the alkylarylene group is interrupted by one or more —S—S— groups;
(f) $C_7$-$C_{40}$ alkylheteroarylene, wherein the alkylheteroarylene group comprises one, two or three heteroatoms independently selected from O, N and S and/or wherein the alkylheteroarylene group is optionally substituted, and/or wherein an alkyl part of the alkylheteroarylene group is linear or branched and is optionally (partly) unsaturated and/or is optionally interrupted by one or more heteroatoms, wherein the heteroatoms are independently selected from O, N and S, and/or wherein an alkyl part of the alkylheteroarylene group is interrupted by one or more —S—S— groups; and
(g) a group wherein two $C_7$-$C_{40}$ (hetero)arylene groups and/or $C_7$-$C_{40}$ alkyl(hetero)arylene groups are connected to each other by a —S—S— group, wherein the alkyl part of the alkyl(hetero)arylene group is linear or branched and is optionally (partly) unsaturated and/or is optionally interrupted by one or more heteroatoms, wherein the heteroatoms are independently selected from O, N and S;

$R^3$ is independently selected from the group consisting of:
(a) H;
(b) $C_1$-$C_{10}$ alkyl, wherein the alkyl group may be linear or branched and is optionally substituted and/or is optionally (partly) unsaturated and/or is optionally interrupted by one, two or three heteroatoms, wherein the heteroatoms are independently selected from O, N and S;
(c) $C_3$-$C_{12}$ cycloalkyl, wherein the cycloalkyl group is optionally substituted and/or is optionally (partly) unsaturated and/or optionally comprises one, two or three heteroatoms in the ring, wherein the heteroatoms are independently selected from O, N and S;
(d) $C_6$-$C_{12}$ aryl, wherein the aryl group is optionally substituted;
(e) $C_6$-$C_{12}$ heteroaryl, wherein the heteroaryl group comprises one, two or three heteroatoms, wherein the heteroatoms are independently selected from O, N and S, and wherein the heteroaryl group is optionally substituted;
(f) $C_7$-$C_{14}$ alkylaryl wherein the alkylaryl group is optionally substituted and/or wherein an alkyl part of the alkylarylene group is linear or branched and is optionally (partly) unsaturated and/or is optionally interrupted by one, two or three heteroatoms, wherein the heteroatoms are independently selected from O, N and S; and
(g) $C_7$-$C_{14}$ alkylheteroaryl, wherein the alkylheteroaryl group comprises one, two or three heteroatoms independently selected from O, N and S and/or wherein the alkylheteroarylene group is optionally substituted, and/or wherein an alkyl part of the alkylheteroarylene group is linear or branched and is optionally (partly) unsaturated and/or is optionally interrupted by one, two or three heteroatoms, wherein the heteroatoms are independently selected from O, N and S;

$R^4$ is independently selected from the group consisting of:
(a) H;
(b) $C_1$-$C_{10}$ alkyl, wherein the alkyl group may be linear or branched;
(c) $C_3$-$C_{12}$ cycloalkyl;
(d) $C_6$-$C_{14}$ aryl;
(e) $C_6$-$C_{14}$ heteroaryl, wherein the alkylheteroaryl group comprises one, two or three heteroatoms independently selected from O, N and S;

(f) $C_7$-$C_{14}$ alkylaryl; and
(g) $C_7$-$C_{14}$ alkylheteroaryl, wherein the alkylheteroaryl group comprises one, two or three heteroatoms independently selected from O, N and S;

$R^5$ is independently selected from the group consisting of:
(a) $C_1$-$C_{12}$ alkylene, wherein the alkylene group may be linear or branched and is optionally substituted and/or is optionally (partly) unsaturated and/or is optionally interrupted by one or more heteroatoms, wherein the heteroatoms are independently selected from O, N and S;
(b) $C_3$-$C_{12}$ cycloalkylene, wherein the cycloalkylene group is optionally substituted and/or is optionally (partly) unsaturated and/or optionally comprises one or more heteroatoms in the ring, wherein the heteroatoms are independently selected from O, N and S;
(c) $C_6$-$C_{12}$ arylene, wherein the arylene group is optionally substituted;
(d) $C_6$-$C_{12}$ heteroarylene, wherein the heteroarylene group comprises one, two or three heteroatoms independently selected from O, N and S and/or wherein the heteroarylene group is optionally substituted;
(e) $C_7$-$C_{12}$ alkylarylene wherein the alkylarylene group is optionally substituted and/or wherein an alkyl part of the alkylarylene group is linear or branched and is optionally (partly) unsaturated and/or is optionally interrupted by one or more heteroatoms, wherein the heteroatoms are independently selected from O, N and S; and
(f) $C_7$-$C_{12}$ alkylheteroarylene, wherein the alkylheteroarylene group comprises one, two or three heteroatoms independently selected from O, N and S and/or wherein the alkylheteroarylene group is optionally substituted, and/or wherein an alkyl part of the alkylheteroarylene group is linear or branched and is optionally (partly) unsaturated and/or is optionally interrupted by one or more heteroatoms, wherein the heteroatoms are independently selected from O, N and S;

POL represents a polymeric core having a weight average molecular weight $M_w$ of about 300 to about 25000;
a=2-64; and
b=1-50.

The present invention further relates to a nanoparticle according to the general Formulas (3) and (4):

one or more heteroatoms, wherein the heteroatoms are independently selected from O, N and S, and/or wherein the alkylene group is interrupted by one or more —S—S— groups; or
(b) $C_3$-$C_{40}$ cycloalkylene, wherein the cycloalkylene group is optionally substituted and/or is optionally (partly) unsaturated and/or optionally comprises one or more heteroatoms in the ring, wherein the heteroatoms are independently selected from O, N and S, and/or wherein the cycloalkylene group is interrupted by one or more —S—S— groups outside the ring; and FG is a Functional Group.

The present invention further relates to a nanogel comprising a PA (PolyAcryl) polymer according to the general Formulas (1) or (2), wherein the nanogel is formed by cross-linking the PA polymer.

The present invention further relates to nanogels having a modified surface.

The present invention further relates to nanogels comprising a biologically active component.

The present invention further relates to the use of the nanogels and the use of the nanogels in the delivery of a biologically active component to a mammal.

The present invention further relates to pharmaceutical compositions comprising the nanogel and a pharmaceutically acceptable carrier.

The present invention further relates to a method for delivering a biologically active component to a mammal, wherein a nanogel or a composition comprising such a nanogel is administered to a mammal.

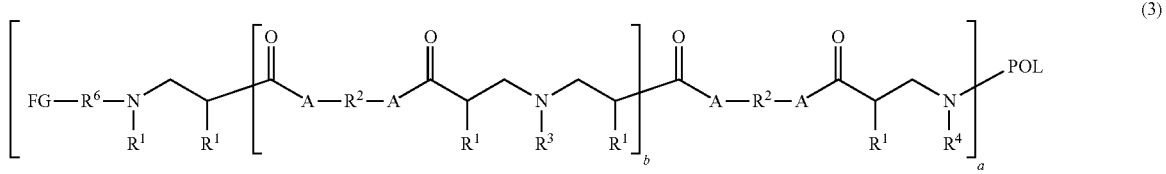

(3)

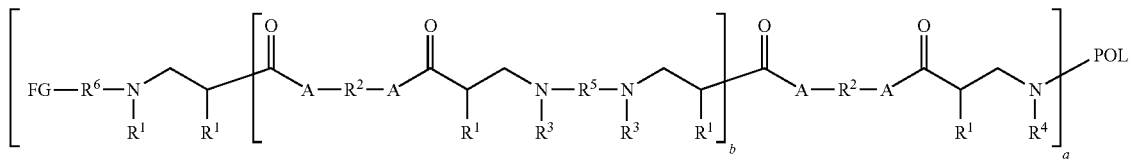

(4)

Figure 4:
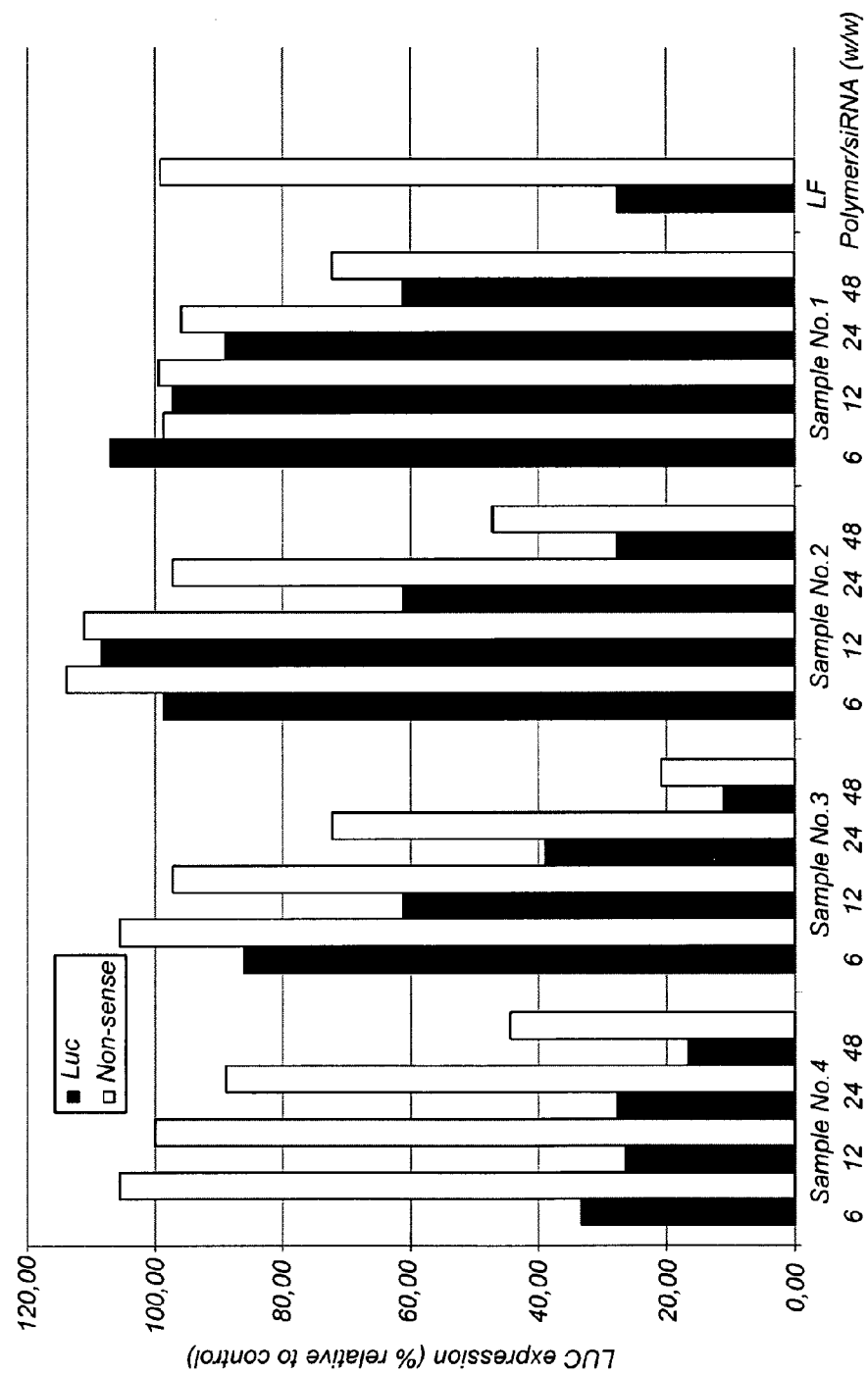

wherein $R^1$, $R^2$, $R^3$, $R^4$, $R^5$, A, POL, a and b are as defined above, and wherein $R^6$ is selected from the group consisting of:

(a) $C_1$-$C_{40}$ alkylene, wherein the alkylene group may be linear or branched and is optionally substituted and/or is optionally (partly) unsaturated and/or is optionally interrupted by FIG. 4 shows the gene silencing efficiency in H1299 cells of PA polymers. The dark grey bars show the percentage of luciferase expression. The light grey bars are the controls with non-sensitive siRNA.

Figure 5:
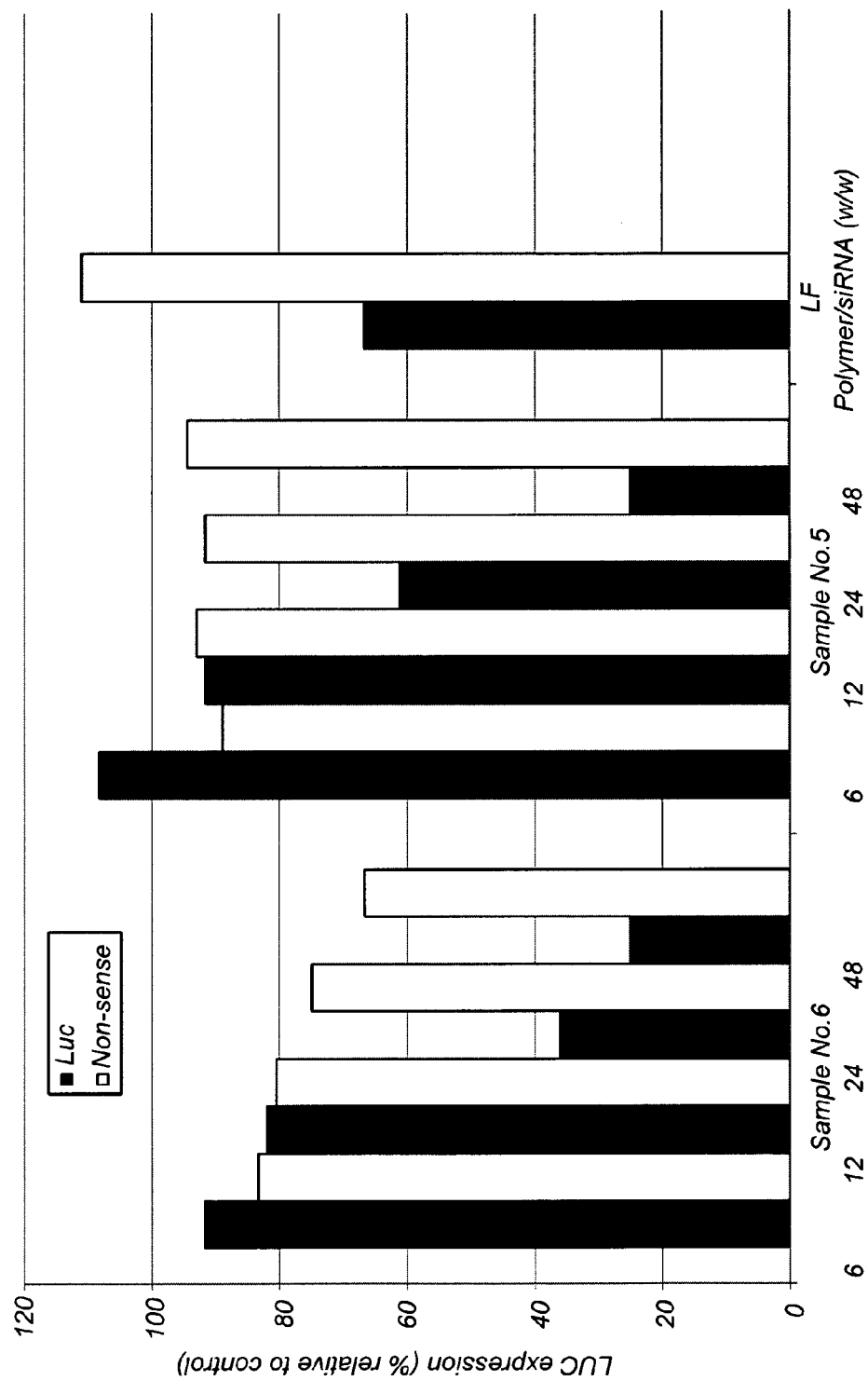

FIG. 5 shows the gene silencing efficiency in H1299 cells of PA polymers.

Figure 6:
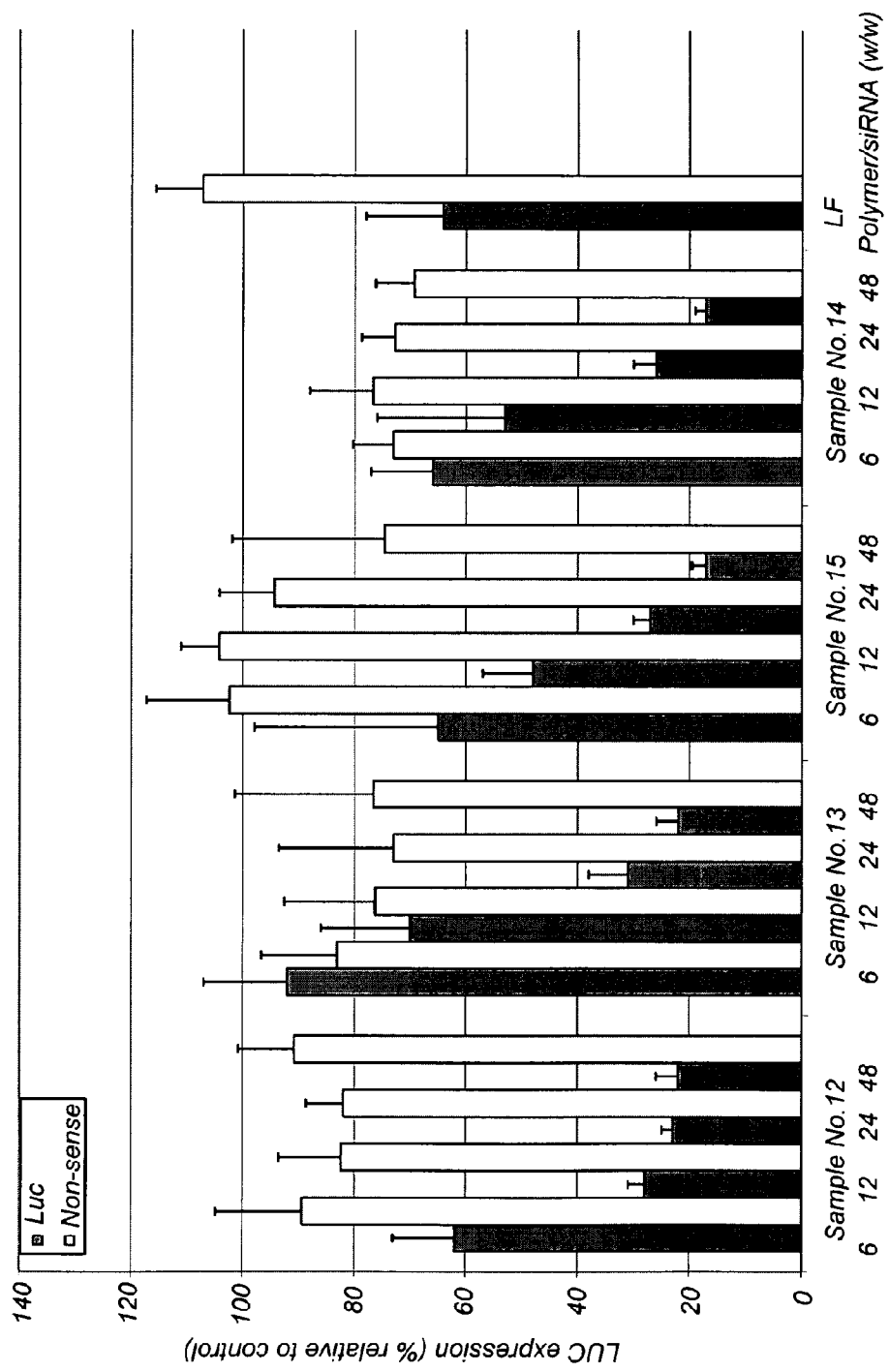

FIG. 6 shows the gene silencing efficiency of some nanogels with different core composition.

Figure 7:
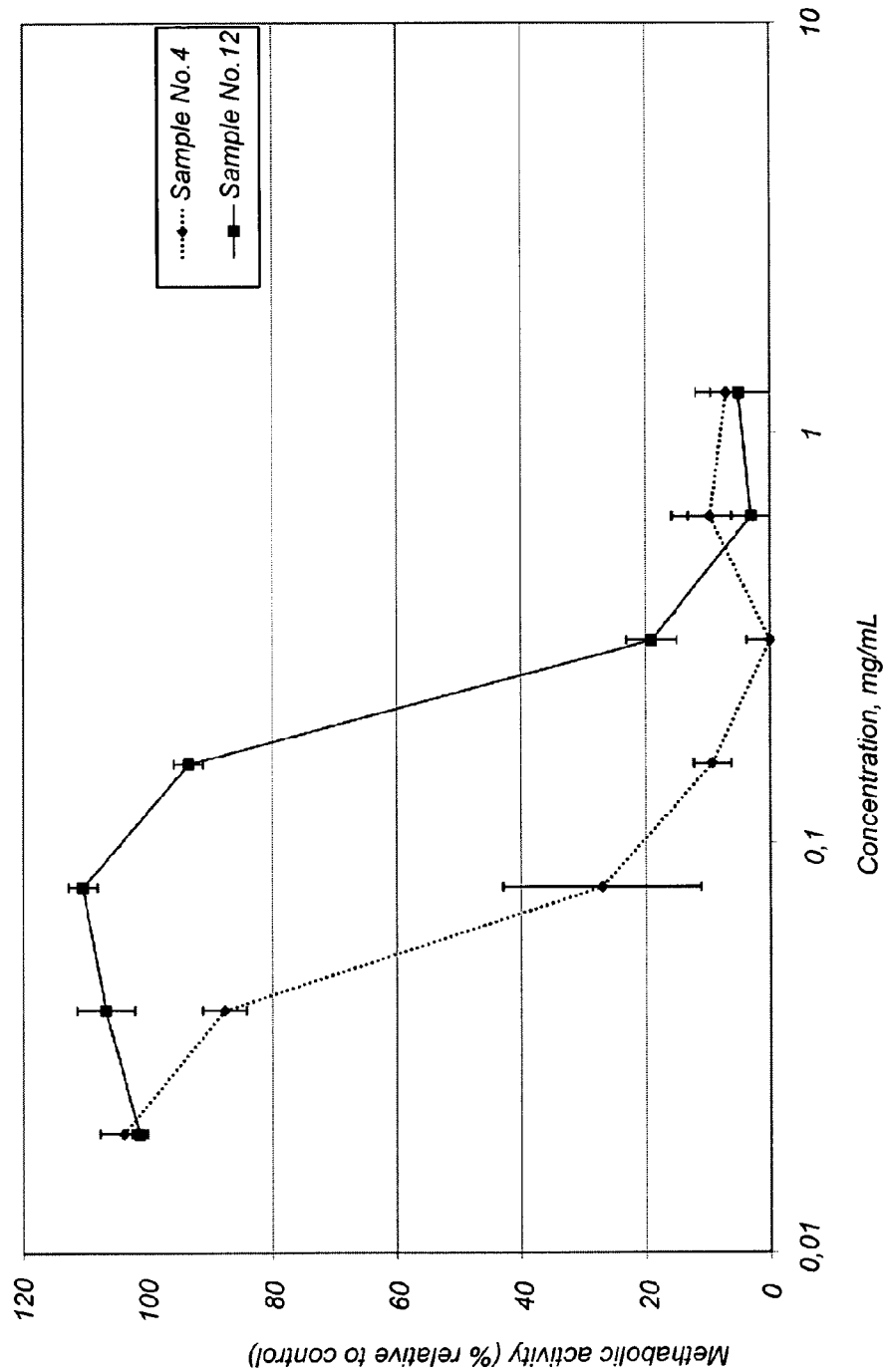

FIG. 7 shows cell viability curves of H1299 cells for a PA polymer (Sample No. 4) and a nanogel (Sample No. 12) as a function of concentration.

Figure 8:
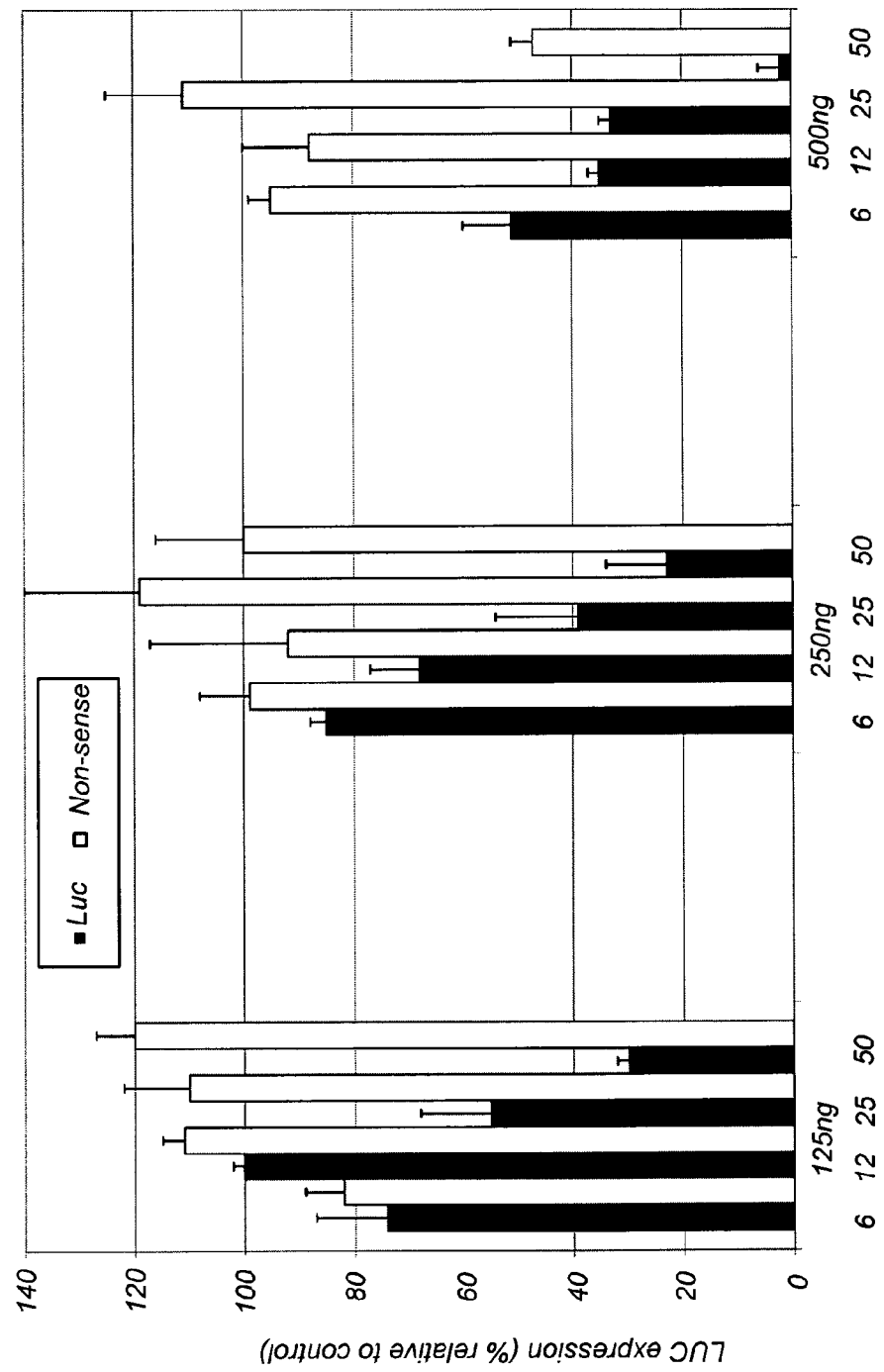

FIG. 8 shows luciferase silencing of H1299 cells under serum conditions by siRNA-loaded nanogels at different polymer/siRNA ratios (w/w) and different doses of siRNA (ng per 100 µL transfection medium).

Figure 9:
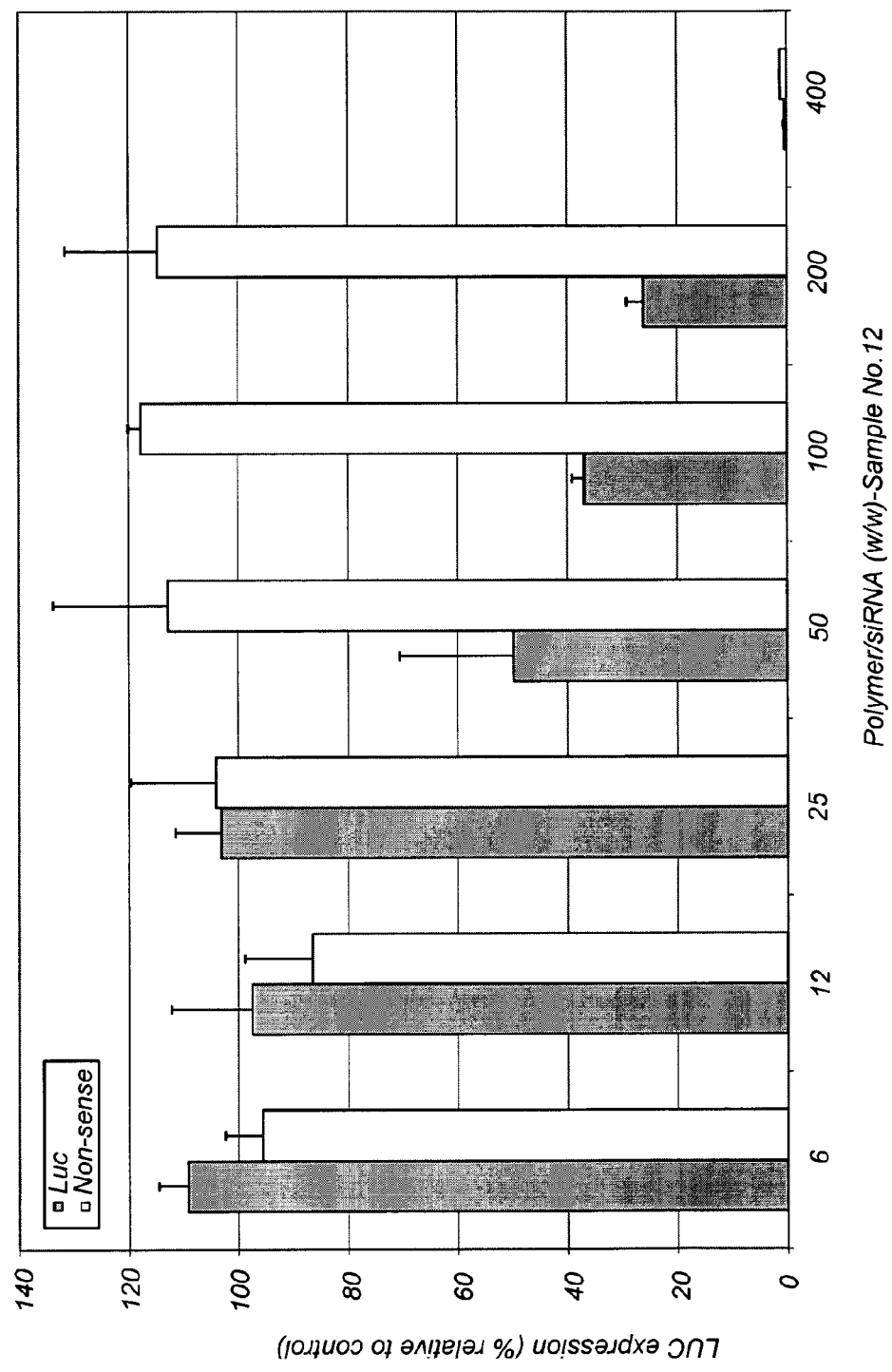

FIG. 9 shows luciferase silencing of H1299 cells under serum conditions by siRNA-loaded nanogels (siRNA 72 nM) at different polymer/siRNA mixing ratios.

Figure 10:
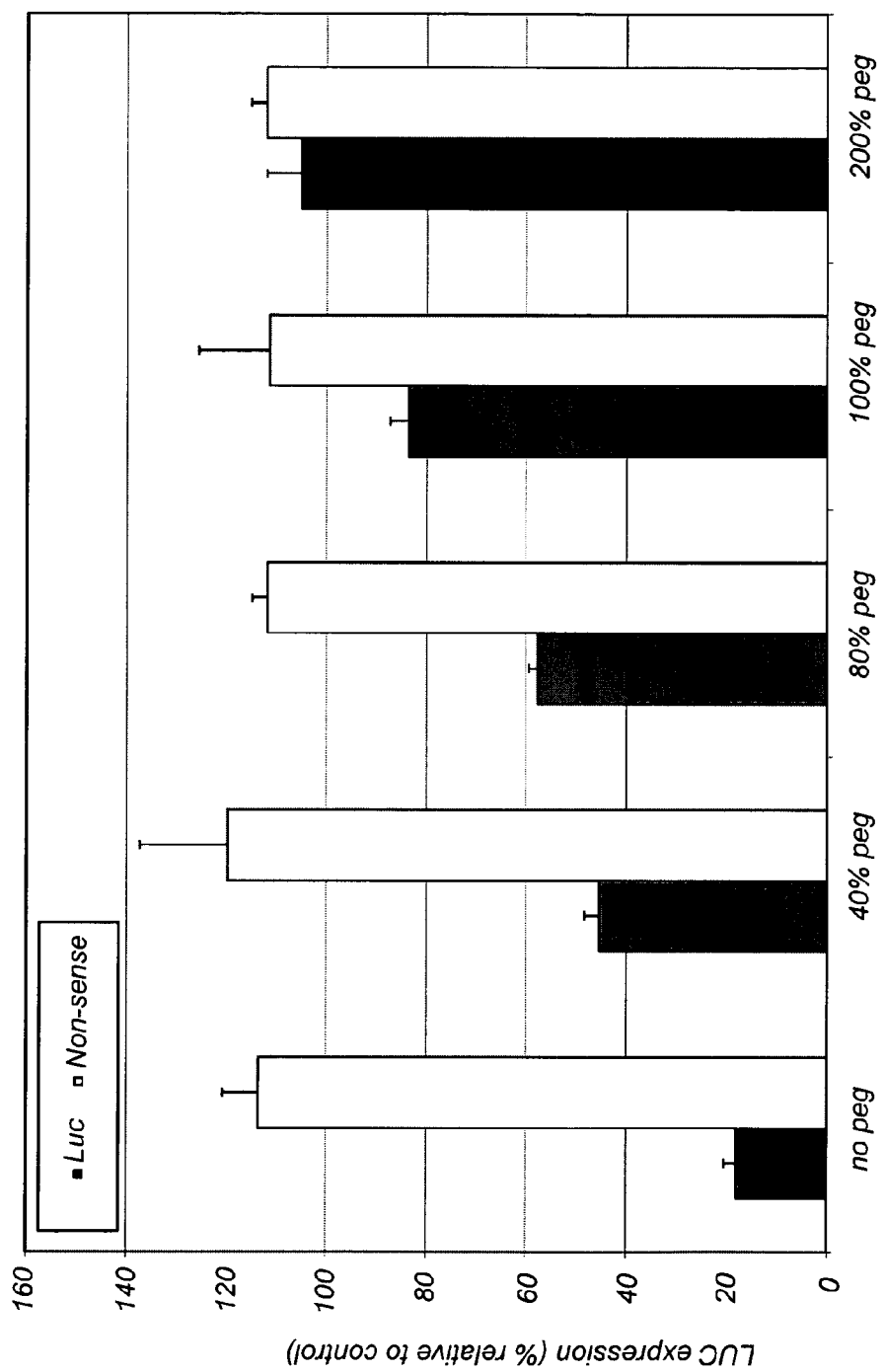

FIG. 10 shows luciferase silencing of H1299 cells by a siRNA-loaded nanogel (Sample No. 12) having its surface modified with amount of PEG (weight % relative to polymer of the nanogel).

FIG. 11 shows luciferase silencing of H1299 cells by a siRNA-loaded nanogel (Sample No. 12), using a freshly prepared siRNA-nanogel solution, a freeze-thawed siRNA-nanogel solution, and a freeze dried siRNA-nanogel solution, respectively. The black bar gives the luciferase expression (set to 100%) of the control experiments, using non-sense coding siRNA. It is shown that the three differently treated formulations with antisense siRNA show equal luciferase silencing activity.

DETAILED DESCRIPTION OF THE INVENTION

The verb "to comprise" as is used in this description and in the claims and its conjugations is used in its non-limiting sense to mean that items following the word are included, but items not specifically mentioned are not excluded. In addition, reference to an element by the indefinite article "a" or "an" does not exclude the possibility that more than one of the element is present, unless the context clearly requires that there is one and only one of the elements. The indefinite article "a" or "an" thus usually means "at least one".

The term "siRNA" encompasses also "miRNA" (micro RNA).

The PA Polymer

According to the present invention, it is preferred that the polymer according to Formulas (1) and (2) has a weight average molecular weight $M_w$ in the range of about 10000 to about 1000000, more preferably in the range of about 20000 to about 500000 g/mol.

According to a preferred embodiment, A is $N(R^1)$ or O, most preferably $N(R^1)$.

According to another preferred embodiment of the present invention, $R^1$ is H.

According to yet another preferred embodiment, $R^2$ is selected from:
(a1) $C_1$-$C_{20}$ alkylene, preferably $C_2$-$C_{12}$ alkylene, wherein the alkylene group may be linear or branched and is optionally substituted and/or is optionally (partly) unsaturated and/or is optionally interrupted by one or more heteroatoms, wherein the heteroatoms are independently selected from O, N and S, and/or wherein the alkylene group is interrupted by one or more —S—S— groups;
(b1) $C_3$-$C_{20}$ cycloalkylene, preferably $C_5$-$C_{12}$ cycloalkylene, wherein the cycloalkylene group is optionally substituted and/or is optionally (partly) unsaturated and/or optionally comprises 1, 2 or 3 heteroatoms in the ring, wherein the heteroatoms are independently selected from O, N and S, and/or wherein the cycloalkylene group is interrupted by one or more —S—S— groups outside the ring;
(c1) $C_6$-$C_{20}$ arylene, preferably $C_6$-$C_{12}$ arylene, wherein the arylene group is optionally substituted;
(d1) $C_6$-$C_{20}$ heteroarylene, preferably $C_6$-$C_{12}$ heteroarylene, wherein the heteroarylene group comprises 1, 2 or 3 heteroatoms independently selected from O, N and S and/or wherein the heteroarylene group is optionally substituted;
(e1) $C_7$-$C_{20}$ alkylarylene, preferably $C_7$-$C_{12}$ alkylheteroarylene wherein the alkylarylene group is optionally substituted and/or wherein an alkyl part of the alkylarylene group is linear or branched and is optionally (partly) unsaturated and/or is optionally interrupted by 1, 2 or 3 heteroatoms, wherein the heteroatoms are independently selected from O, N and S, and/or wherein an alkyl part of the alkylarylene group is interrupted by one or more —S—S— groups;
(f1) $C_7$-$C_{20}$ alkylheteroarylene, preferably $C_7$-$C_{12}$ alkylheteroarylene, wherein the alkylheteroarylene group comprises 1-3 heteroatoms independently selected from O, N and S and/or wherein the alkylheteroarylene group is optionally substituted, and/or wherein an alkyl part of the alkylheteroarylene group is linear or branched and is optionally (partly) unsaturated and/or is optionally interrupted by one or more heteroatoms, wherein the heteroatoms are independently selected from O, N and S, and/or wherein an alkyl part of the alkylheteroarylene group is interrupted by one or more —S—S— groups; and
(g1) a group wherein two $C_7$-$C_{20}$ (hetero)arylene groups and/or $C_7$-$C_{20}$ alkyl(hetero)arylene groups, preferably two $C_7$-$C_{12}$ (hetero)arylene groups and/or $C_7$-$C_{12}$ alkyl(hetero)arylene groups, are connected to each other by a —S—S— group, wherein the alkyl part of the alkyl(hetero)arylene group is linear or branched and is optionally (partly) unsaturated and/or is optionally interrupted by one or more heteroatoms, wherein the heteroatoms are independently selected from O, N and S.

According to another preferred embodiment of the present invention, $R^2$ is selected from group (a1) or group (b1), more preferably group from group (a1), and in particular from group (a1) wherein the $C_1$-$C_{40}$ alkylene group is interrupted by one or more —S—S— groups.

According to a preferred embodiment, when $R^3$ is substituted $C_1$-$C_{10}$ alkyl, the alkyl group is substituted by a group selected from —OH, —$OR^7$, —$NH_2$; —$NH(R^7)$, —$N(R^7)_2$, —$C(O)OR^7$, —$C(O)R^7$, —$C(O)NHR^7$, and —$C(O)NR^7_2$, wherein $R^7$ is independently selected from the group consisting of:
(a) H;
(b) $C_1$-$C_{10}$ alkyl, wherein the alkyl group may be linear or branched and is optionally substituted and/or is optionally (partly) unsaturated and/or is optionally interrupted by one, two or three heteroatoms, wherein the heteroatoms are independently selected from O, N and S;
(c) $C_3$-$C_{12}$ cycloalkyl, wherein the cycloalkyl group is optionally substituted and/or is optionally (partly) unsaturated and/or optionally comprises one, two or three heteroatoms in the ring, wherein the heteroatoms are independently selected from O, N and S;
(d) $C_6$-$C_{12}$ aryl, wherein the aryl group is optionally substituted;
(e) $C_6$-$C_{12}$ heteroaryl, wherein the heteroaryl group comprises one, two or three heteroatoms independently selected from O, N and S and/or wherein the heteroaryl group is optionally substituted;
(f) $C_7$-$C_{14}$ alkylaryl wherein the alkylaryl group is optionally substituted and/or wherein an alkyl part of the alkylarylene group is linear or branched and is optionally (partly) unsaturated and/or is optionally interrupted by one, two or three heteroatoms, wherein the heteroatoms are independently selected from O, N and S; and (g) $C_7$-$C_{14}$ alkylheteroaryl, wherein the alkylheteroaryl group comprises one, two or three heteroatoms independently selected from O, N and S and/or wherein the alkylheteroarylene group is optionally substituted, and/or wherein an alkyl part of the alkylheteroarylene group is linear or branched and is optionally (partly) unsaturated and/or is optionally interrupted by one, two or three heteroatoms, wherein the heteroatoms are independently selected from O, N and S.

According to a preferred embodiment, when $R^3$ is substituted $C_3$-$C_{12}$ cycloalkyl, the cycloalkyl group has a pending group selected from —OH, —$OR^7$, —$NH_2$; —$NH(R^7)$, —$N(R^7)_2$, —$C(O)OR^7$, —$C(O)R^7$, —$C(O)NHR^7$, and —$C(O)NR^7_2$, wherein $R^7$ is as defined above.

According to a preferred embodiment, when $R^3$ is substituted $C_6$-$C_{12}$ aryl, $C_6$-$C_{12}$ heteroaryl, $C_7$-$C_{14}$ alkylaryl or $C_7$-$C_{14}$ alkylheteroaryl, the alkylaryl or alkylheteroaryl group is substituted with, preferably with one, two or three of —OH, —$OR^7$, —$NH_2$; —$NH(R^7)$, —$N(R^7)_2$, —$C(O)OR^7$, —$C(O)R^7$, —$C(O)NHR^7$, and —$C(O)NR^7_2$, wherein $R^7$ is as defined above.

In the PA polymer according to the present invention which is represented by general Formulas (1) and (2), the polymeric core POL is preferably based on or is selected from a branched, hyperbranched, multi-arm, dentritic or star-type (co)polymer, said (co)polymer preferably having 2-64, more preferably 2-32, even more preferably 2-16 terminal amino groups, preferably primary amino groups. Accordingly, a is 2-64, preferably 2-32 and in particular 2-16. The (co)polymers may comprise different linear or branched spacers which comprise one or more heteroatoms selected from the group consisting of O, N and S, preferably O and N.

According to the present invention, b is 1-50, preferably 1-30 and in particular 1-10.

It is well known in the art that dendritic (co)polymers are not always perfectly branched and may therefore have a hyperbranched structure. The degree of branching (DB) can be defined by:

$$DB = \frac{(D+T)}{(D+L+T)}$$

wherein D is the number of dendritic, L the number of linear and T the number of terminal units. Perfect dendrimers will have a DB of 1, whereas hyperbranched (co)polymers have typically a DB of 0.4 to 0.5 up to even 0.9. In this patent application, the term "dendrimer" is to be understood as including "perfectly branched dendrimers" as well as "imperfectly branched dendrimers" which are also referred to as "hyperbranched (co)polymers". Alternatively, the term "hyperbranched (co)polymers" may also comprise "true" hyperbranched (co)polymers. That is, that these macromolecules are purposively prepared as having a hyperbranched structure. The term "dendrimer" is to be understood as comprising both dendrimeric homopolymers and dendrimeric copolymers. The term "copolymer" includes polymers made of at least two different monomers.

Hyperbranched polymers can be obtained from the random polymerization of monomers in the presence of at least one polyfunctional monomer capable of introducing branching. Such a synthetic scheme is shown by Hawker and Devonport in "Step-Growth Polymers for High-Performance Materials: New Synthetic Methods," Hedrick, J. L. and Labadie, J. W., Eds., Am. Chem. Soc., Washington, D.C., 1996, pp. 191-193. Hult et al., in "Advances in Polymer Science," Vol. 143 (1999), Roovers, J., Ed., Springer, New York, pp. 1-34, present a review of hyperbranched polymers.

Highly branched dendritic polymers are for example discussed in "Polymeric Materials Encyclopedia", Vol. 5 (1996), J. C. Salamone, Ed., CRC Press, New York, pp. 3049-3053. Dendritic polymers have generally a non-linear architecture and are intrinsically globular in shape. Discrete, stepwise synthetic methods are used to prepare highly branched pure compounds or dendrimers. As discussed by Hawker and Devonport in "Step-Growth Polymers for High-Performance Materials: New Synthetic Methods", Hedrick, J. L. and Labadie, J. W., Eds., Am. Chem. Soc., Washington, D.C., 1996, pp. 186-196, if the macromolecule has highly regular branching which follows a strict geometric pattern, it is a dendrimer. Dendrimers are typically monodisperse and are prepared in a multi-step approach with purifications at each stage. The architecture of dendrimers is also discussed by Roovers and Comanita in "Advances in Polymer Science", Vol. 142 (1999), Roovers, J., Ed., Springer, New York, pp. 179-228. Dendrimers consist of a core molecule which defines the centre of symmetry of the molecule, and branching layers. Tomalia et al., Angew. Chem. Int. Ed. Eng., 29 (1990), 138-175 disclose "starburst" dendrimers which consist of an initiator core and branching groups.

Preferably, the polymer core POL is based on PEI (commercially available from e.g. Denditrech, Inc.), Astramol® polymers (DSM), JEFFAMINE® polymers (Huntsman), PAMAM polymers (sometimes also called PANAM polymers), PPI polymers, PEAN polymers and PEAC polymers. The term "PEI" refers to polyethyleneimines. The term "PAMAM" refer to poly(amido amine) polymers which are commercially available under de trade name Starburst®. The term "PPI" means polypropylene imine polymers. The term "PEAN" refers to poly(ester amine) polymers. The term "PEAC" refers to poly(ether amine) polymers. All these polymers are well known in the art. Accordingly, it is preferred that the polymer core POL is based on or is selected from the group consisting of PEI, PAMAM, PPI, PEAN and PEAC.

According to the present invention, it is preferred that the weight average molecular weight $M_w$ of the polymer core POL is about 300 to about 5000, more preferably about 600 to about 5000.

Preferred polymers used for the polymer core POL are the polymers (polyether amines) of the JEFFAMINE® T series which are commercially available with a weight average molecular weight $M_w$ in the range of about 440 to about 5000. Suitable types of JEFFAMINE® T polymers include T-403 ($M_w$=440) and T-3000 ($M_w$=3000).

Another group of preferred polymers that can be used for the polymer core POL are PEI's. PEI can have either a linear or branched structure. Linear PEI is commercial available (jetPEI, Polyplus-Transfection Co.; Exgen 500, Fermentas Co.) and is usually prepared by hydrolysis of poly(2-ethyl-2-oxazoline). Branched PEI's are prepared from aziridine and these polymers have a highly branched structure and comprise about 25% primary amine groups, about 50% secondary amine groups, and about 25% tertiary amine groups. Preferably, the PEI has a weight average molecular weight $M_n$ of about 600 to about 3000, more preferably about 600 to about 2000. Linear PEI's may be represented by the general Formula (5a):

(5a)

Branched PEI's may be represented by the general Formula (5b):

(5b)

$$\left[ H_2N \begin{array}{c} NH_2 \\ | \\ N \end{array} \begin{array}{c} H \\ | \\ N \end{array} \begin{array}{c} NH_2 \\ | \\ N \end{array} \begin{array}{c} H \\ | \\ N \end{array} \begin{array}{c} NH_2 \\ | \\ N \end{array} NH_2 \right]_n$$

wherein n is such that the PEI has a weight average molecular weight $M_n$ of about 300 to about 5000, more preferably about 300 to about 3000, even more preferably about 600 to about 2500. Such PEI's are for example available from Sigma-Aldrich.

Yet another group of preferred polymers used for the polymer core POL are poly(amido amine) hyperbranched polymers and dendrimers, preferably those of the 1$^{st}$ to the 4$^{th}$ generation, more preferably of the 1st and/or the 3$^{rd}$ generation. These polymers are commercially available from Dentritech, Inc., and have a weight average molecular weight $M_w$ in the range of about 1400 (1$^4$ generation) to about 15000 (4$^{th}$ generation).

Yet another group of preferred polymers used for the polymer core POL are the polymers represented by the general Formulas (6)-(9):

$$N(R^8)_{3-n}[(CR^9{}_2)_m N(R^{10}R^{11})]_n \quad (6)$$

$$[(R^{10}R^{11})N-(CR^9{}_2)_m]_2 N-P-N[(CR^9{}_2)_m-N(R^{10}R^{11})]_2 \quad (7)$$

$$N(R^8)_{3-n}[(CR^9{}_2)_m-C(O)N(R^9)-(CR^9{}_2)_m-N(R^{12}R^{13})]_n \quad (8)$$

$$[(R^{12}R^{13})N-(CR^9{}_2)_m-N(R^9)C(O)-(CR^9{}_2)_m]_2 N-P-N[(CR^9{}_2)-C(O)NH-(CR^9{}_2)_m-N(R^{12}R^{13})]_2 \quad (9)$$

wherein:
$R^8$ is a hydrogen atom, a linear or branched $C_1$-$C_{20}$ alkyl group or a $-[(CR^{14}{}_2)_q-X]_o-R^{15}$ group, wherein X is O or $N(R^8)$;
m is 2, 3 or 4;
n is 2 or 3;
o is 1-10;
q is 2, 3 or 4;
P is $-(CR^9{}_2)_m-$, a $C_6$-$C_{12}$ arylene group, a $C_6$-$C_{12}$ cycloalkylene group or a $-[(CR^{14}{}_2)_q-X]_p-C(R^{14})_2]-$ group, wherein X is O or $N(R^8)$ and p is 1-10;
$R^9$ is a hydrogen atom or a linear or branched $C_1$-$C_6$ alkyl group;
$R^{10}$ and $R^{11}$ are independently a hydrogen atom, a linear or branched $C_1$-$C_6$ alkyl group or a group of the formula $-(CR^{14}{}_2)_q NR^{16}R^{17}$, provided that $R^{10}$ and $R^{11}$ are not both a linear or branched $C_1$-$C_6$ alkyl group;
$R^{16}$ and $R^{17}$ are independently a hydrogen atom, a linear or branched $C_1$-$C_6$ alkyl group or a group of the formula $-(CR^{14}{}_2)_q NR^{18}R^{19}$, provided that $R^{16}$ and $R^{17}$ are not both a linear or branched $C_1$-$C_6$ alkyl group;
$R^{18}$ and $R^{19}$ are independently a hydrogen atom, a linear or branched $C_1$-$C_6$ alkyl group or a group of the formula $-(CR^{14}{}_2)_q NR^{20}R^{21}$, provided that $R^{18}$ and $R^{19}$ are not both a linear or branched $C_1$-$C_6$ alkyl group;
$R^{20}$ and $R^{21}$ are independently a hydrogen atom or a linear or branched $C_1$-$C_6$ alkyl group, provided that $R^{20}$ and $R^{21}$ are not both a linear or branched $C_1$-$C_6$ alkyl group;
$R^{22}$ is a hydrogen atom or a methyl group, provided that at least one $R^{22}$ is a hydrogen atom;
$R^{15}$ is a hydrogen or linear or branched $C_1$-$C_{20}$ alkyl group or a $-[(CR^{14}{}_2)_q-X]_o-R^{15}$ group as defined above;
$R^{12}$ and $R^{13}$ are independently a hydrogen atom, a linear or branched $C_1$-$C_6$ alkyl group or a group of the formula $-(CR^9{}_2)_m-C(O)NH-(CR^9{}_2)_m-N(R^{23}R^{24})$; provided that $R^{12}$ and $R^{13}$ are not both a linear or branched $C_1$-$C_6$ alkyl group;
$R^{23}$ and $R^{24}$ are independently a hydrogen atom, a linear or branched $C_1$-$C_6$ alkyl group or a group of the formula $-(CR^9{}_2)_m-C(O)NH-(CR^9{}_2)_m-N(R^{25}R^{26})$, provided that $R^{23}$ and $R^{24}$ are not both a linear or branched $C_1$-$C_6$ alkyl group;
$R^{25}$ and $R^{26}$ are independently a hydrogen atom, a linear or branched $C_1$-$C_6$ alkyl group or a group of the formula $-(CR^9{}_2)_m-C(O)NH-(CR^9{}_2)_m-N(R^{27}R^{28})$, provided that $R^{25}$ and $R^{26}$ are not both a linear or branched $C_1$-$C_6$ alkyl group;
$R^{27}$ and $R^{28}$ are independently a hydrogen atom or a linear or branched $C_1$-$C_6$ alkyl group, provided that $R^{27}$ and $R^{28}$ are not both a linear or branched $C_1$-$C_6$ alkyl group.

In Formulas (6)-(9), a preferred group polymers used for the polymer core POL is the group wherein:
$R^8$ and $R^{15}$ is a hydrogen atom or a $-[(CR^{14}{}_2)_q-X]_o-R^{15}$ group, wherein X is NH;
$R^9$, $R^{20}$, $R^{21}$, and $R^{21}$ are a hydrogen atom;
$R^{10}$ and $R^{11}$ are independently a hydrogen atom or a group of the formula $-(CR^{14}{}_2)_q NR^{16}R^{17}$;
$R^{16}$ and $R^{17}$ are independently a hydrogen atom or a group of the formula $-(CR^{14}{}_2)_q NR^{18}R^{19}$;
$R^{18}$ and $R^{19}$ are independently a hydrogen atom or a group of the formula $-(CR^{14}{}_2)_q NR^{20}R^{21}$;
$R^{12}$ and $R^{13}$ are independently a hydrogen atom or a group of the formula $-(CR^9{}_2)_m-C(O)NH-(CR^9{}_2)_m-N(R^{23}R^{24})$;
$R^{23}$ and $R^{24}$ are independently a hydrogen atom or a group of the formula $-(CR^9{}_2)_m-C(O)NH-(CR^9{}_2)_m-N(R^{25}R^{26})$;
$R^{25}$ and $R^{26}$ are independently a hydrogen atom or a group of the formula $-(CR^9{}_2)_m-C(O)NH-(CR^9{}_2)_m-N(R^{27}R^{28})$; and
$R^{27}$ and $R^{28}$ are independently a hydrogen atom.

In Formulas (6)-(9), it is also preferred that m and q is 2:
A more preferred class of the PA polymers according to the present invention can be represented by general Formulas (10) and (11):

(10)

$$\left[ \left[ \begin{array}{c} O \\ \| \\ =\!\!\!\!\!\!\!\!\!\!\!\!\!\!\!\!\!\!\!\!\!\!-Y-(CR^{29}{}_2)_r-Z-(CR^{29}{}_2)_r-Y-\underset{R^1}{\overset{O}{\|}}-\underset{R^{30}}{N}-\underset{R^1}{\|}- \\ R^1 \end{array} \right]_b \left[ \begin{array}{c} O \\ \| \\ Y-(CR^{29}{}_2)_r-Z-(CR^{29}{}_2)_r-Y-\underset{R^1}{\overset{O}{\|}}-\underset{R^{31}}{N}- \end{array} \right]_a POL \right.$$

(11)

$$\left[\begin{array}{c}\begin{array}{c}O\\\|\\\end{array}\\\begin{array}{c}\\R^1\end{array}\end{array}Y-(CR^{29}_2)_r-Z-(CR^{29}_2)_r-Y\begin{array}{c}O\\\|\\\end{array}\begin{array}{c}\\R^1\end{array}\begin{array}{c}\\N-R^{32}-N\\R^{30}\quad R^{30}\end{array}\begin{array}{c}O\\\|\\\end{array}\begin{array}{c}\\R^1\end{array}\right]_b Y-(CR^{29}_2)_r-Z-(CR^{29}_2)_r-Y\begin{array}{c}O\\\|\\\end{array}\begin{array}{c}\\R^1\end{array}\begin{array}{c}\\N\\R^{31}\end{array}POL\right]_a$$

wherein:

$R^1$ is independently selected from H and $CH_3$;
Y is O or $N(R^1)$;
r is 2, 3 or 4;
Z is —S—S—;
$R^{29}$ is independently selected from the group consisting of:
(a) H;
(b) $C_1$-$C_{10}$ alkyl, wherein the alkyl group may be linear or branched and is optionally substituted and/or is optionally (partly) unsaturated and/or is optionally interrupted by 1, 2 or 3 heteroatoms, wherein the heteroatoms are independently selected from O, N and S;
(c) $C_3$-$C_{12}$ cycloalkyl, wherein the cycloalkyl group is optionally substituted and/or is optionally (partly) unsaturated and/or optionally comprises 1, 2 or 3 heteroatoms in the ring, wherein the heteroatoms are independently selected from O, N and S;
(d) $C_6$-$C_{12}$ aryl, wherein the aryl group is optionally substituted;
(e) $C_6$-$C_{12}$ heteroaryl, wherein the heteroaryl group comprises 1, 2 or 3 heteroatoms independently selected from O, N and S and/or wherein the heteroaryl group is optionally substituted;
(f) $C_7$-$C_{14}$ alkylaryl wherein the alkylaryl group is optionally substituted and/or wherein an alkyl part of the alkylarylene group is linear or branched and is optionally (partly) unsaturated and/or is optionally interrupted by 1, 2 or 3 heteroatoms, wherein the heteroatoms are independently selected from O, N and S; and
(g) $C_7$-$C_{14}$ alkylheteroaryl, wherein the alkylheteroaryl group comprises 12 or 3 heteroatoms independently selected from O, N and S and/or wherein the alkylheteroarylene group is optionally substituted, and/or wherein an alkyl part of the alkylheteroarylene group is linear or branched and is optionally (partly) unsaturated and/or is optionally interrupted by 1, 2 or 3 heteroatoms, wherein the heteroatoms are independently selected from O, N and S; the alkylheteroaryl group optionally being substituted, preferably with 1, 2 or 3 of —OH, —OR$^{29}$, —NH$_2$; —NH(R$^{29}$) or —N(R$^{29}$)$_2$;

$R^{30}$ is independently selected from the group consisting of:
(a) H;
(b) $C_1$-$C_{10}$ alkyl, wherein the alkyl group may be linear or branched and is optionally substituted and/or is optionally (partly) unsaturated and/or is optionally interrupted by one, two or three heteroatoms, wherein the heteroatoms are independently selected from O, N and S;
(c) $C_3$-$C_{12}$ cycloalkyl, wherein the cycloalkyl group is optionally substituted and/or is optionally (partly) unsaturated and/or optionally comprises one, two or three heteroatoms in the ring, wherein the heteroatoms are independently selected from O, N and S;
(d) $C_6$-$C_{12}$ aryl, wherein the aryl group is optionally substituted;
(e) $C_6$-$C_{12}$ heteroaryl, wherein the heteroaryl group comprises one, two or three heteroatoms independently selected from O, N and S and/or wherein the heteroaryl group is optionally substituted;
(f) $C_7$-$C_{14}$ alkylaryl wherein the alkylaryl group is optionally substituted and/or wherein an alkyl part of the alkylarylene group is linear or branched and is optionally (partly) unsaturated and/or is optionally interrupted by one, two or three heteroatoms, wherein the heteroatoms are independently selected from O, N and S; and
(g) $C_7$-$C_{14}$ alkylheteroaryl, wherein the alkylheteroaryl group comprises one, two or three heteroatoms independently selected from O, N and S and/or wherein the alkylheteroarylene group is optionally substituted, and/or wherein an alkyl part of the alkylheteroarylene group is linear or branched and is optionally (partly) unsaturated and/or is optionally interrupted by one, two or three heteroatoms, wherein the heteroatoms are independently selected from O, N and S;

$R^{31}$ is independently selected from the group consisting of:
(a) H;
(b) $C_1$-$C_{10}$ alkyl, wherein the alkyl group may be linear or branched;
(c) $C_3$-$C_{12}$ cycloalkyl;
(d) $C_6$-$C_{12}$ aryl;
(e) $C_6$-$C_{12}$ heteroaryl, wherein the heteroaryl group comprises one, two or three heteroatoms independently selected from O, N and S;
(f) $C_7$-$C_{14}$ alkylaryl; and
(g) $C_7$-$C_{14}$ alkylheteroaryl, wherein the alkylheteroaryl group comprises one, two or three heteroatoms independently selected from O, N and S;

$R^{32}$ is independently selected from the group consisting of:
(a) $C_1$-$C_{12}$ alkylene, wherein the alkylene group may be linear or branched and is optionally substituted and/or is optionally (partly) unsaturated and/or is optionally interrupted by one or more heteroatoms, wherein the heteroatoms are independently selected from O, N and S;
(b) $C_3$-$C_{12}$ cycloalkylene, wherein the cycloalkylene group is optionally substituted and/or is optionally (partly) unsaturated and/or optionally comprises one or more heteroatoms in the ring, wherein the heteroatoms are independently selected from O, N and S;
(c) $C_6$-$C_{12}$ arylene, wherein the arylene group is optionally substituted;
(d) $C_6$-$C_{12}$ heteroarylene, wherein the heteroarylene group comprises one, two or three heteroatoms independently selected from O, N and S and/or wherein the heteroarylene group is optionally substituted;
(e) $C_7$-$C_{14}$ alkylarylene wherein the alkylarylene group is optionally substituted and/or wherein an alkyl part of the alkylarylene group is linear or branched and is optionally (partly) unsaturated and/or is optionally interrupted by one or more heteroatoms, wherein the heteroatoms are independently selected from O, N and S; and
(f) $C_7$-$C_{14}$ alkylheteroarylene, wherein the alkylheteroarylene group comprises one, two or three heteroatoms independently selected from O, N and S and/or wherein the alkylheteroarylene group is optionally substituted, and/or wherein an alkyl part of the alkylheteroarylene group is linear or branched and is optionally (partly) unsaturated and/or is optionally interrupted by one or more heteroatoms, wherein the heteroatoms are independently selected from O, N and S; and
a=2-64; and
b=1 to 50.

According to a preferred embodiment, when $R^{30}$ is substituted $C_1$-$C_{10}$ alkyl, the alkyl group is substituted by a group selected from —OH, —OR$^7$, —NH$_2$; —NH(R$^7$), —N(R$^7$)$_2$, —C(O)OR$^7$, —C(O)R$^7$, —C(O)NHR$^7$, and —C(O)NR$^7{}_2$, wherein R$^7$ is independently selected from the group consisting of:
(a) H;
(b) C$_1$-C$_{10}$ alkyl, wherein the alkyl group may be linear or branched and is optionally substituted and/or is optionally (partly) unsaturated and/or is optionally interrupted by one, two or three heteroatoms, wherein the heteroatoms are independently selected from O, N and S;
(c) C$_3$-C$_{12}$ cycloalkyl, wherein the cycloalkyl group is optionally substituted and/or is optionally (partly) unsaturated and/or optionally comprises one, two or three heteroatoms in the ring, wherein the heteroatoms are independently selected from O, N and S;
(d) C$_6$-C$_{12}$ aryl, wherein the aryl group is optionally substituted;
(e) C$_6$-C$_{12}$ heteroaryl, wherein the heteroaryl group comprises one, two or three heteroatoms independently selected from O, N and S and/or wherein the heteroaryl group is optionally substituted;
(f) C$_7$-C$_{14}$ alkylaryl wherein the alkylaryl group is optionally substituted and/or wherein an alkyl part of the alkylarylene group is linear or branched and is optionally (partly) unsaturated and/or is optionally interrupted by one, two or three heteroatoms, wherein the heteroatoms are independently selected from O, N and S; and
(g) C$_7$-C$_{14}$ alkylheteroaryl, wherein the alkylheteroaryl group comprises one, two or three heteroatoms independently selected from O, N and S and/or wherein the alkylheteroarylene group is optionally substituted, and/or wherein an alkyl part of the alkylheteroarylene group is linear or branched and is optionally (partly) unsaturated and/or is optionally interrupted by one, two or three heteroatoms, wherein the heteroatoms are independently selected from O, N and S.

According to a preferred embodiment, when R$^{30}$ is substituted C$_3$-C$_{12}$ cycloalkyl, the cycloalkyl group has a pending group selected from —OH, —OR$^7$, —NH$_2$; —NHR$^7$), —N(R$^7$)$_2$, —C(O)OR$^7$, —C(O)R$^7$, —C(O)NHR$^7$, and —C(O)NR$^7{}_2$, wherein R$^7$ is as defined above.

According to a preferred embodiment, when R$^{30}$ is substituted C$_6$-C$_{12}$ aryl, C$_6$-C$_{12}$ heteroaryl, C$_7$-C$_{14}$ alkylaryl or C$_7$-C$_{14}$ alkylheteroaryl, the alkylaryl or alkylheteroaryl group is substituted with, preferably with one, two or three of —OH, —OR$^7$, —NH$_2$; —NH(R$^7$), —N(R$^7$)$_2$, —C(O)OR$^7$, —C(O)R$^7$, —C(O)NHR$^7$, and —C(O)NR$^7{}_2$, wherein R$^7$ is as defined above.

In a more preferred class of the PA polymers according to general Formulas (10) and (11):
R$^1$ is independently selected from H and CH$_3$;
Y is N(R$^1$);
r is 2;
Z is —S—S—;
R$^{29}$ is independently selected from H and C$_1$-C$_{10}$ alkyl, wherein the alkyl group may be linear or branched and is optionally substituted and/or is optionally (partly) unsaturated and/or is optionally interrupted by one or more heteroatoms, wherein the heteroatoms are independently selected from O, N and S;
R$^{30}$ is independently selected from H and C$_1$-C$_{10}$ alkyl, wherein the alkyl group may be linear or branched and is optionally substituted and/or is optionally (partly) unsaturated and/or is optionally interrupted by one, two or three heteroatoms, wherein the heteroatoms are independently selected from O, N and S;
R$^{31}$ is independently selected from H and C$_1$-C$_{10}$ alkyl, wherein the alkyl group may be linear or branched; and
R$^{32}$ is C$_1$-C$_{10}$ alkylene, wherein the alkylene group may be linear or branched and is optionally substituted and/or is optionally (partly) unsaturated and/or is optionally interrupted by one, two or three heteroatoms, wherein the heteroatoms are independently selected from O, N and S.

In an even more preferred class of the PA polymers according to general Formulas (10) and (11):
R$^1$ is H;
Y is N(R$^1$);
r is 2;
Z is —S—S—;
R$^{29}$ is H;
R$^{30}$ is independently selected from H and C$_1$-C$_{10}$ alkyl, wherein the alkyl group is linear and is optionally interrupted by one, two or three heteroatoms, wherein the heteroatoms are independently selected from O, N and S;
R$^{31}$ is H; and
R$^{32}$ is C$_1$-C$_{10}$ alkylene, wherein the alkylene group may be linear or branched.

In yet an even more preferred class of the PA polymers according to general Formulas (10) and (11):
R$^1$ is H;
Y is N(R$^1$);
r is 2;
Z is —S—S—;
R$^{29}$ is H;
R$^{30}$ is C$_1$-C$_{10}$ alkyl, wherein the alkyl group is linear and is optionally interrupted by one, two or three heteroatoms, wherein the heteroatoms are independently selected from O, N and S;
R$^{31}$ is H; and
R$^{32}$ is C$_1$-C$_{10}$ alkylene, wherein the alkyl group may be linear or branched.

In a most preferred class of the PA polymers according to general Formulas (10) and (11):
Y is NH;
r is 2;
Z is —S—S—;
R$^{29}$ is H;
R$^{30}$ is C$_1$-C$_6$ alkyl;
R$^{31}$ is H; and
R$^{32}$ is C$_1$-C$_{10}$ alkylene, wherein the alkylene group is linear.

In all these preferred classes of the PA polymers according to Formulas (10) and (11), it is preferred that when R$^{30}$ is substituted C$_1$-C$_{10}$ alkyl, the alkyl group is substituted by a group selected from —OH, —OR$^7$, —NH$_2$; —NH(R$^7$), —N(R$^7$)$_2$, —C(O)OR$^7$, —C(O)R$^7$, —C(O)NHR$^7$, and —C(O)NR$^7{}_2$, wherein R$^7$ is as defined above. Preferably, the alkyl group is substituted by —OH, —NH$_2$, —NH(R$^7$), or —N(R$^7$)$_2$; more preferably by substituted —OH or —NH$_2$.

Process for Preparing the PA Polymer

According to an embodiment of the present invention, the PA polymers according to the present invention as represented by general Formulas (1) and (2) may be prepared by a process which comprises the steps of:
(1) reacting a monomer (I) according to general Formula (12):

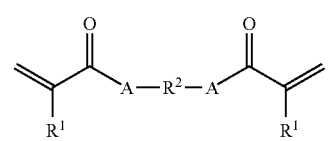
(12)

wherein R$^1$, A and R$^2$ are as defined above, with a monomer (II) according to general Formula (13) or a monomer (III) according to Formula (14):

(H$_2$N)—R$^3$    (13)

HR$^3$N—R$^5$—NR$^3$H    (14)

wherein R$^3$ and R$^5$ are as defined above, in a molar ratio of monomer (I):monomer (II) of from about 1.5:1 to about 10:1 to form a macromer according to general Formulas (15) or (16):

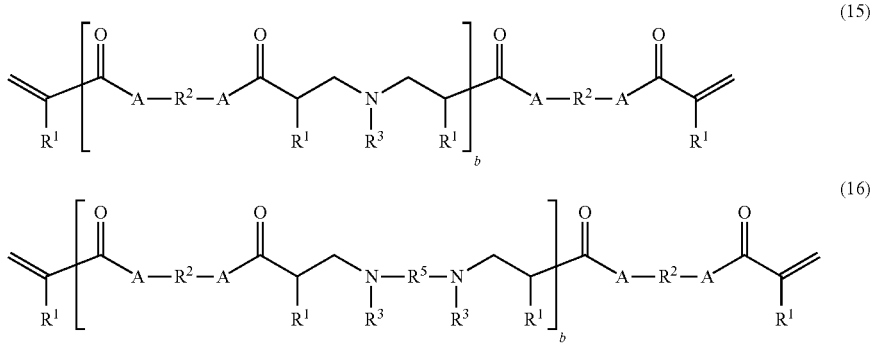

wherein b is as defined above; and (2) reacting the macromer according to general Formulas (15) or (16) with a polymer according to Formula (17);

  (17)

wherein a, POL and $R^4$ are as defined above and wherein at least one $R^4$ is H.

Hence, in this reaction, a —C(O)—C($R^1$)=C group reacts with a ($R^4{}_2$)N group of POL under the formation of a —C(O)—CH($R^1$)—CH$_2$—N($R^4$)— moiety (Michael addition) as will be clear to the person skilled in the art.

wherein $R^1$, Y, $R^{29}$ and r are as defined above, with a monomer (IV) according to general Formula (19) or a monomer (V) according to Formula (20):

  (19)

  (20)

wherein $R^{30}$ and $R^{32}$ are as defined above, in a molar ratio of monomer (I):monomer (II) of from about 1.5:1 to about 10:1 to form a macromer according to general Formulas (21) or (22):

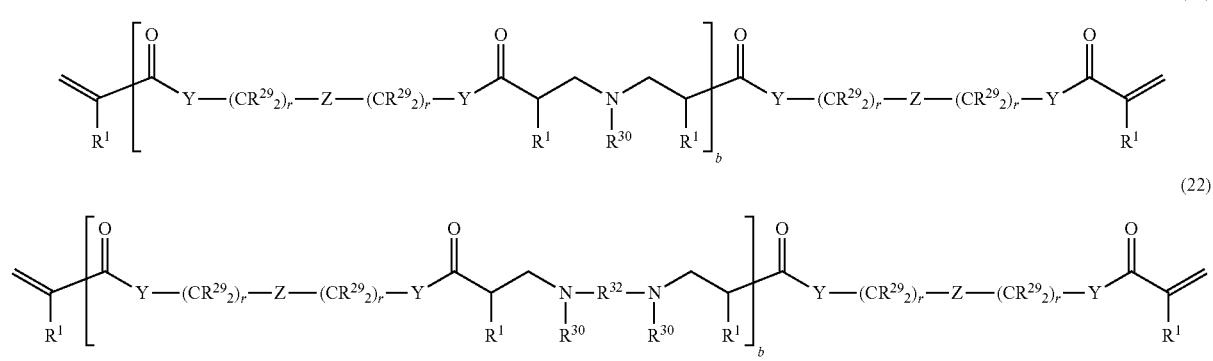

wherein b is as defined above; and (2) reacting the macromer according to general Formulas (21) or (22) with a polymer according to Formula (23);

  (23)

wherein a, POL and $R^{31}$ are as defined above and wherein at least one $R^{31}$ is H.

According to the present invention, it is preferred that step (1) of the process is performed at a temperature ranging from ambient temperature to about 100° C., preferably from about 30° to about 80° C.

According to the present invention, it is preferred that step (2) of the process is performed at a temperature ranging from ambient temperature to about 100° C., preferably from about 30° to about 80° C.

The Nanoparticle

The present invention also relates to a nanoparticle. The nanoparticle according to the present invention is represented by the general Formulas (3) and (4):

Accordingly, the present invention also relates to PA polymer according to general Formulas (1) and (2) which is obtainable by this process.

According to a preferred embodiment of the present invention, the PA polymers according to the present invention as represented by general Formulas (10) and (11) may also be prepared by this process which comprises the steps of:

(1) reacting a monomer (III) according to general Formula (18):

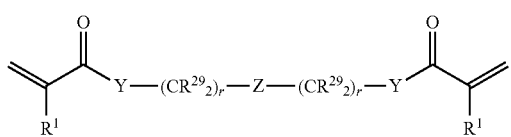  (18)

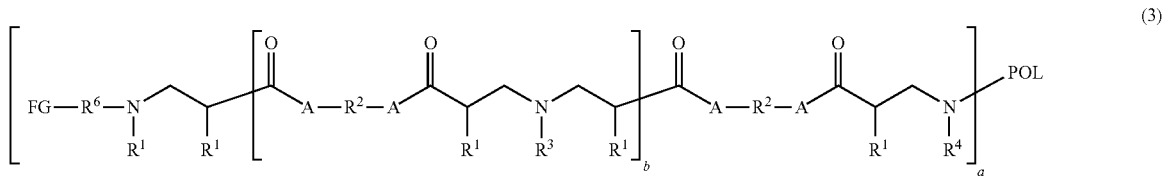

(3)

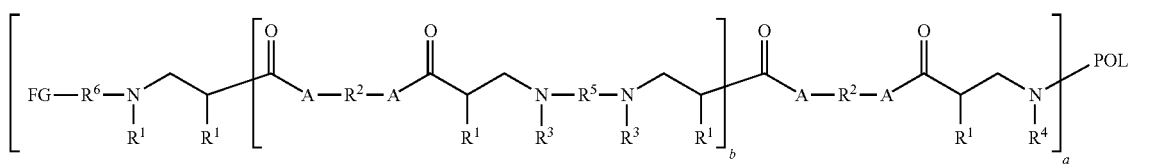

(4)

wherein $R^1$, $R^2$, $R^3$, $R^4$, $R^5$, $R^6$, A, POL, FG, a and b are as described above.

According to a preferred embodiment, the nanoparticle is represented by general Formulas (24) and (25):

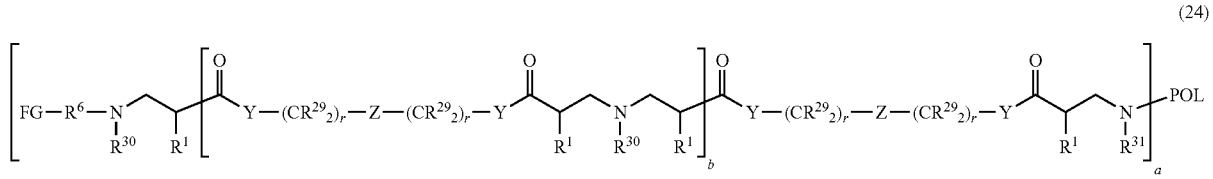

(24)

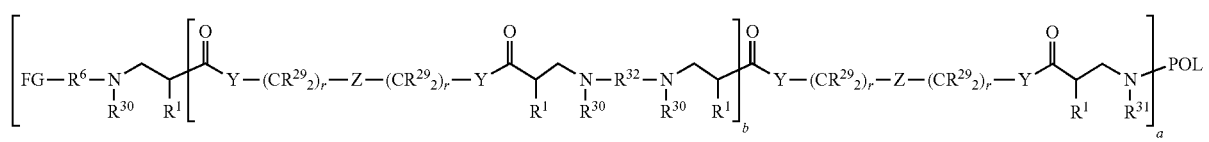

(25)

wherein $R^1$, $R^6$, $R^{29}$, $R^{30}$, $R^{31}$, $R^{32}$, Y, Z, POL, FG, a, b and r as defined above.

The functional group FG is a substituent that is capable of forming a covalent bond with a complementary functional group (CFG) of a reagent for post-modification. The group FG is preferably selected from functional groups that enable the formation of a covalent bond with a group CFG, preferably under biocompatible reaction conditions, in particular under conditions of physiological pH and ambient temperature and in aqueous systems. Such groups FG are well known to the person skilled in the art. In particular, the group FG is selected from the group consisting of a group selected from —OH, —OR$^7$, —NH$_2$; —NH(R$^7$), —N(R$^7$)$_2$, —C(O)OR$^7$, —C(O)R$^7$, —C(O)NHR$^7$, and —C(O)NR$^7{}_2$, wherein $R^7$ is independently selected from the group consisting of:

(a") H;

(b") $C_1$-$C_{10}$ alkyl, wherein the alkyl group may be linear or branched and is optionally substituted and/or is optionally (partly) unsaturated and/or is optionally interrupted by one, two or three heteroatoms, wherein the heteroatoms are independently selected from O, N and S;

(c") $C_3$-$C_{12}$ cycloalkyl, wherein the cycloalkyl group is optionally substituted and/or is optionally (partly) unsaturated and/or optionally comprises one, two or three heteroatoms in the ring, wherein the heteroatoms are independently selected from O, N and S;

(d") $C_6$-$C_{12}$ aryl, wherein the aryl group is optionally substituted;

(e") $C_6$-$C_{12}$ heteroaryl, wherein the heteroaryl group comprises one, two or three heteroatoms independently selected from O, N and S and/or wherein the heteroaryl group is optionally substituted;

(f") $C_7$-$C_{14}$ alkylaryl wherein the alkylaryl group is optionally substituted and/or wherein an alkyl part of the alkylarylene group is linear or branched and is optionally (partly) unsaturated and/or is optionally interrupted by one, two or three heteroatoms, wherein the heteroatoms are independently selected from O, N and S; and (g") $C_7$-$C_{14}$ alkylheteroaryl, wherein the alkylheteroaryl group comprises one, two or three heteroatoms independently selected from O, N and S and/or wherein the alkylheteroarylene group is optionally substituted, and/or wherein an alkyl part of the alkylheteroarylene group is linear or branched and is optionally (partly) unsaturated and/or is optionally interrupted by one, two or three heteroatoms, wherein the heteroatoms are independently selected from O, N and S.

The CFG is preferably selected from the group consisting of —OH, —OR$^7$, —NH$_2$; —NH(R$^7$), —N(R$^7$)$_2$, —C(O)OR$^7$, —C(O)R$^7$, —C(O)NHR$^7$, and —C(O)NR$^7{}_2$, wherein $R^7$ is as defined above for FG. For example, the FG may be —OH and the CFG may be —COOH.

The nanoparticles according to general Formulas (3), (4), (24) and (25) may be prepared by a process wherein a PA polymer according to general Formulas (1), (2), (10) or (11), respectively, are reacted with a reagent according to Formula (26a) or Formula (26b):

FG-R$^6$—NHR$^{30}$ (26a)

FG-R$^6$—SH (26b)

wherein FG and $R^6$ are as defined above, FG optionally being hydrogen. Other useful FG's include biologically or pharmacologically active groups, e.g. oligo- and polypeptides. Suitable examples for the reagents according to Formula (26a) and (26b) are ethylene diamine, diethylene triamine, triethylene tetramine, tetraethylene pentamine, 1,6-diamino hexane, amine terminated PEG, amine terminated PPO, thiol terminated PEG and thiol terminated PPO.

However, as will be apparent to those skilled in the art, the reagent according to Formula (26b) can not only react with the acrylate groups of the PA polymers according to any one of Formulas (1), (2), (10) and (11), but also with the —S—S— groups (when present) in $R^2$ of the PA polymer according to Formula (1) or Formula (2) or with the —S—S— group as represented by Z in the PA polymers according to Formula (10) or Formula (11). Additionally, since $R^3$ of the PA polymer according to Formula (1) or Formula (2) and $R^{30}$ of the PA polymer according to Formula (10) or Formula (11) may comprise functional groups, it can also be envisaged that the reagent according to Formula (26a) can react with these functional groups. Furthermore, instead of the reagent according to Formula (26a), also reagents according to the Formula FG-$R^6$—RG can be used, wherein RG is selected from the group consisting of —OH, —$OR^7$, —C(O)$OR^7$, —C(O)$R^7$, —C(O)$NHR^7$, —C(O)$NR^7_2$ and —$SO_2Cl$, wherein $R^7$ is as defined above, when $R^3$ and $R^{30}$ comprise e.g. a primary or secondary amino group.

The Nanogel

The present invention also relates to a nanogel. The nanogels according to the present invention have as important advantages that they are stable in dissolved and dispersed form. The nanogels according to the present invention are also storage stable. The solutions of the nanogels can be frozen without losing their integrity and can be freeze-dried to a powder form which can easily be restituted to a solution without loss of activity or integrity.

The nanogel is prepared by cross-linking the PA polymer according to general Formulas (1) and (2), wherein the cross-linking is preferably conducted by UV radiation, preferably UV radiation with a wave length of about 365 nm. The cross-linking reaction is preferably performed in the presence of a photo-initiator. The cross-linking reaction is also preferably performed in a water-in-oil emulsion. It is further preferred that the cross-linking reaction is performed at a pH of less than 7, preferably less than about 6. Preferably, the pH is higher than about 1, preferably higher than about 2.

The present invention therefore also relates to a nanogel which is obtainable by the above described process which comprises the step of cross-linking a PA polymer according to general Formulas (1), (2), (10 and (11), preferably by subjecting the PA polymer to UV radiation.

Loaded Nanogels

According to the invention, it is preferred that the nanogel further comprises a biologically active component selected from the group of RNA (in particular siRNA) or derivatives or fragments hereof, DNA or derivatives or fragments hereof, (oligo)peptides and derivatives thereof, and proteins and derivatives thereof.

The loading of the nanogel is performed by contacting the biologically active component with the nanogel in an aqueous solvent system, preferably a buffered aqueous solvent system, wherein the aqueous solvent system preferably has a physiological pH. Methods for loading the nanogels are known in the art.

Surface Modification of the Nanogels

The nanogel according to the present invention, either in loaded form or in unloaded form, may be further functionalised by post-modification.

According to a preferred embodiment of the post-modification, the nanogel that is obtainable by cross-linking PA polymers according to Formulas (1) or (2), wherein $R^3$ is independently selected from the group consisting of:

(a1) substituted $C_1$-$C_{10}$ alkyl, wherein the alkyl group may be linear or branched and is optionally (partly) unsaturated and/or is optionally interrupted by one, two or three heteroatoms, wherein the heteroatoms are independently selected from O, N and S;

(b1) substituted $C_3$-$C_{12}$ cycloalkyl, wherein the cycloalkyl group is optionally (partly) unsaturated and/or optionally comprises one, two or three heteroatoms in the ring, wherein the heteroatoms are independently selected from O, N and S;

(c1) substituted $C_6$-$C_{12}$ aryl;

(d1) substituted $C_6$-$C_{12}$ heteroaryl, wherein the heteroaryl group comprises one, two or three heteroatoms, wherein the heteroatoms are independently selected from O, N and S;

(e1) substituted $C_7$-$C_{14}$ alkylaryl wherein an alkyl part of the alkylarylene group is linear or branched and is optionally (partly) unsaturated and/or is optionally interrupted by one, two or three heteroatoms, wherein the heteroatoms are independently selected from O, N and S;

(f1) substituted $C_7$-$C_{14}$ alkylheteroaryl, wherein the alkylheteroaryl group comprises one, two or three heteroatoms independently selected from O, N and S and/or wherein an alkyl part of the alkylheteroarylene group is linear or branched and is optionally (partly) unsaturated and/or is optionally interrupted by one, two or three heteroatoms, wherein the heteroatoms are independently selected from O, N and S;

wherein the above groups (a)-(f) comprise a functional group (FG) as a substituent that is capable of forming a covalent bond with a complementary functional group (CFG) of a reagent for post-modification R and wherein the nanogels optionally comprise a biologically active component, is reacted with said reagent R according to the process:

nanogel-FG+R—CFG

The group CFG is capable of forming a covalent bond with the group FG. Suitable examples for groups FG and CFG are well known to the person skilled in the art. For example, the FG can be a —COOH group whereas the CFG group is a —$NH_2$ group.

According to a preferred embodiment, the functional group FG is selected from the group consisting of a group selected from —OH, —$OR^7$, —$NH_2$; —$NH(R^7)$, —$N(R^7)_2$, —C(O)$OR^7$, —C(O)$R^7$, —C(O)$NHR^7$, and —C(O)$NR^7_2$, wherein $R^7$ is independently selected from the group consisting of:

(a") H;

(b") $C_1$-$C_{10}$ alkyl, wherein the alkyl group may be linear or branched and is optionally substituted and/or is optionally (partly) unsaturated and/or is optionally interrupted by one, two or three heteroatoms, wherein the heteroatoms are independently selected from O, N and S;

(c") $C_3$-$C_{12}$ cycloalkyl, wherein the cycloalkyl group is optionally substituted and/or is optionally (partly) unsaturated and/or optionally comprises one, two or three heteroatoms in the ring, wherein the heteroatoms are independently selected from O, N and S;

(d") $C_6$-$C_{12}$ aryl, wherein the aryl group is optionally substituted;

(e") $C_6$-$C_{12}$ heteroaryl, wherein the heteroaryl group comprises one, two or three heteroatoms independently selected from O, N and S and/or wherein the heteroaryl group is optionally substituted;

(f') $C_7$-$C_{14}$ alkylaryl wherein the alkylaryl group is optionally substituted and/or wherein an alkyl part of the alkylarylene group is linear or branched and is optionally (partly) unsaturated and/or is optionally interrupted by one, two or three heteroatoms, wherein the heteroatoms are independently selected from O, N and S; and (g") $C_7$-$C_{14}$ alkylheteroaryl, wherein the alkylheteroaryl group comprises one, two or three heteroatoms independently selected from O, N and S and/or wherein the alkylheteroarylene group is optionally substituted, and/or wherein an alkyl part of the alkylheteroarylene group is linear or branched and is optionally (partly) unsaturated and/or is optionally interrupted by one, two or three heteroatoms, wherein the heteroatoms are independently selected from O, N and S.

According to another preferred embodiment of the post-modification, the nanogel that is obtainable by cross-linking PA polymers according to Formulas (10) or (11), is reacted with a reagent for post-modification R' according to the process:

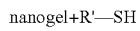

The groups R and R' are preferably 2-thioethyl, 2-hydroxyethyl, and PEG (polyethylene oxide) residues or PPO (polypropylene oxide) residues having a number average molecular weight $M_n$ of about 500 to about 10000. As will apparent to those skilled in the art, the reagent R'—SH can also react with the —S—S— groups (when present) in the nanogel as is descrived above for PA polymers according to Formulas (1), (2) (10) and Formula (11).

The present invention therefore further relates to surface modified nanogels which are obtainable by a first process comprising the steps of:
(1) cross-linking a PA polymer according to general Formulas (1), (2), (10) or (11), preferably by subjecting the PA polymer to UV radiation to form a nanogel;
(2) optionally loading the nanogel with a biologically active component selected from the group of RNA (in particular siRNA) or derivatives or fragments hereof, DNA or derivatives or fragments hereof, (oligo)peptides and derivatives thereof, and proteins and derivatives thereof; and
(3) reacting the nanogel with a reagent R-CFG or R'—SH.

The surface modified nanogels are also obtainable by a second process comprising the steps of:
(1') cross-linking a PA polymer according to general Formulas (1), (2), (10) or (11), preferably by subjecting the PA polymer to UV radiation to form a nanogel;
(2') reacting the nanogel with a reagent R-CFG or R'—SH; and
(3') optionally loading the nanogel with a biologically active component selected from the group of RNA (in particular siRNA) or derivatives or fragments hereof, DNA or derivatives or fragments hereof, (oligo)peptides and derivatives thereof, and proteins and derivatives thereof.

The surface modified nanogels are also obtainable by a third process comprising the steps of:
(1") reacting the nanogel with a reagent R-CFG or R'—SH thereby forming a functionalized nanogel;
(2") cross-linking the functionalized nanogel, preferably by subjecting the functionalized nanogel to UV radiation to form a nanogel; and
(3") optionally loading the nanogel with a biologically active component selected from the group of RNA (in particular siRNA) or derivatives or fragments thereof, DNA or derivatives or fragments thereof, (oligo)peptides and derivatives thereof, and proteins and derivatives thereof.

In the step (1) of the first process and step (1') of the second process, not all acrylate groups need to be cross-linked so that non-cross-linked acrylate groups can be functionalized in step (3) of the first process and step (2) of the second process, respectively. Likewise, in step (1") of the third process, not all acrylate groups need to be functionalized to that non-cross-linked acrylate groups can still be cross-linked. Accordingly, the product obtained in either of these three processes may be very complex. According to the present invention, it is even preferred that when first a functionalization step is carried out not all of the acrylate groups are functionalized thereby enabling further cross-linking of the remaining acrylate groups. Likewise, it is also preferred when first a cross-linking step is carried out not all acrylate groups are cross-linked thereby enabling further functionalization of the remaining acrylate groups. A person skilled in the art will be well capable to select appropriate reaction conditions, in particular by selecting appropriate molar ratios of reactants and starting materials, to control the degree of cross-linking and functionalization. In addition, and as described above, there are other reactive groups within the PA polymers, e.g. —S—S— groups, that may be functionalized in conjunction with the acrylate groups.

Applications

The nanogels according to the present invention are very suitable as drug-delivery carriers because of their high loading capacity, high stability, and responsiveness to environmental factors, such as ionic strength, reduction potential, pH and temperature. In particular, the nanogels according to the present invention have additional benefits for delivery of biologically active components over self-assembled polymeric nanoparticulate systems as delivery vehicles, since in the case of these nanogels all polymeric constituents are incorporated into the delivery nanogel whereas in the self-assembled polymeric nanoparticulate systems usually excess of free polymer in solution is needed due to the equilibrium conditions. This frequently causes undesired cytotoxicity effects and upon dilution of the formulation destabilisation of the nanoparticles.

EXAMPLES

Materials and Methods

Cystamine bisacrylamide (CBA, Polysciences, USA) was purchased in the highest purity grade and used without further purification. Low molecular polyethylene imine (PEI) with weight average molecular weight 800 Da (PEI800) was obtained from Aldrich. A photoinitiator Igracure 2959 was purchased from Ciba. ABIL EM 90 surfactant was purchased from Degussa-Goldschmidt (Evonik). Anti-luciferase siRNA was purchased from Eurogentec, AllStars Negative Control siRNA was purchased from Qiagen. All other chemicals were purchased from Aldrich. All reagents and solvents were of reagent grade and were used without further purification. NMR spectra were recorded on Varian Unity 300 ($^1$H NMR 300 MHz) using tetramethylsilane (TMS) as the internal standard.

Example 1

Synthesis of Diacryloyl Macromer (A-(CBA-ABOL)$_n$-A)

Approximately 0.48 g (0.0054 mol.) of 4-amino-1-butanol (ABOL) and 1.56 g (0.006 mol) of CBA (9/10 mol/mol ABOL/CBA ratio) was added to 3 ml of a solution of CaCl$_2$ (0.4 M) in methanol-water 3/1 (v/v) and the reaction flask was sealed. The polymerization was carried out at 50° C. and the reaction was allowed to proceed for 30 h, yielding a viscous solution. The reaction was monitored by following with $^1$H-NMR, the integrated areas of two acryloyl peaks (δ 5.55 and 6.05) and two methylene peaks of the butanol side groups (1.58 ppm and 1.78 ppm). At the end of the polymerization the NMR integrations indicated that the macromer (A-(CBA-ABOL)$_n$-A) contained about six ABOL units per acryloyl group, i.e. n=12.

Example 2

Synthesis of Hyperbranched p(CBA-ABOL/PEI)

A volume of 2.12, 1.06, 0.53 or 0.26 ml of a solution of low molecular PEI 800 (100 mg/ml) was added to 1.34 g A-p(CBA-ABOL)$_{12}$-A diacryloyl macromer in 3 ml methanol-water 3/1 (v/v) in order to achieve a desired molar ratio of acryloyl groups to PEI of 3/1, 6/1, 12/1 and 24/1, respectively. The mixture was diluted with a 0.4 M solution of CaCl$_2$ in methanol-water 3/1 (v/v) to a final PEI concentration of 10 mM in order to prevent gelation during the reaction. The reaction was carried out at 50 C for 24 h. Subsequently, one half of the reaction mixture containing p(CBA-ABOL)/PEI end-capped with CBA acryloyl groups was separated for the synthesis of the nanogels. To the second half of the reaction mixture a 10-fold excess of ethylenediamine (EDA) was added in order to transform all terminal CBA acryloyl groups into amines. The resulting solution of ethylenediamine end-capped p(CBA-ABOL)/PEI was diluted with water to about 30 ml, acidified with 4 M HCl to pH~4, and then purified using a ultrafiltration membrane (MWCO 1000 g/mol). After freeze-drying, the EDA-terminated hyperbranched (CBA-ABOL)/PEI polymer was collected as the HCl-salt. Yield 30-50%. The ABOL/Acryloyl ratios for different p(CBA-ABOL)/PEI's are summarised in Table 1.

TABLE 1

|  | p(CBA-ABOL)/ PEI-13% | p(CBA-ABOL)/ PEI-7% | p(CBA-ABOL)/ PEI-4% | p(CBA-ABOL)/ PEI-2% |
|---|---|---|---|---|
| Sample No. | 1 | 2 | 3 | 4 |
| Content of PEI in feed, wt % | 13 | 7 | 4 | 2 |
| Acryloyl/PEI (mol/mol) in feed | 3 | 6 | 12 | 24 |
| Remaining ABOL/ Acryloyl (mol/mol) in p(CBA-ABOL)/PEI | >100 | 30 | 18 | 13 |

Example 3

Synthesis of Hyperbranched p(CBA-ABOL)/PAMAM

A volume of 1.16, 0.87 or 0.58 ml of a solution of second generation PAMAM dendrimer (G2) (100 mg/ml) was added to 1.34 g A-p(CBA-ABOL)$_{12}$-A diacryloyl macromer in 3 ml methanol-water 3/1 (v/v) in order to achieve a desired molar ratio of acryloyl groups to PAMAM molecules of 10/1, 15/1 and 20/1, respectively. The mixture was diluted by a 0.4 M solution of $CaCl_2$ in methanol-water 3/1 (vol./vol.) to a PAMAM final concentration of 10 mM in order to prevent gelation during reaction. The reaction was carried out at 50° C. for 24 h. Subsequently, one half of the reaction mixture containing p(CBA-ABOL)/PAMAM end-capped with CBA acryloyl groups was separated for the synthesis of nanogels. To the second half of the reaction mixture a 10-fold excess of ethylenediamine (EDA) was added in order to transform all terminal CBA acryloyl groups into amines. The resulting solution of ethylenediamine end-capped p(CBA-ABOL)/PAMAM was diluted with water to about 30 ml, acidified with 4 M HCl to pH~4, and then purified using a ultrafiltration membrane (MWCO 1000 g/mol). After freeze-drying, the EDA-terminated hyperbranched p(CBA-ABOL)/PAMAM polymer was collected as the HCl-salt. Yield 30-50%. The ABOL/Acryloyl ratios for different p(CBA-ABOL)/PAMAM compositions are summarised ion Table 2

TABLE 2

|  | p(CBA-ABOL)/ PAMAM-8% | p(CBA-ABOL)/ PAMAM-6% | p(CBA-ABOL)/ PAMAM-4% |
|---|---|---|---|
| Sample No. | 5 | 6 | 7 |
| Content of PAMAM in feed (wt %) | 8 | 6 | 4 |
| Acryloyl/PAMAM in feed (mol/mol) | 10 | 15 | 20 |

TABLE 2-continued

|  | p(CBA-ABOL)/ PAMAM-8% | p(CBA-ABOL)/ PAMAM-6% | p(CBA-ABOL)/ PAMAM-4% |
|---|---|---|---|
| Remaining ABOL/ Acryloyl in p(CBA-ABOL)/ PAMAM (mol/mol) | 23 | 14 | 13 |

Example 4

Synthesis of EDA-Terminated Hyperbranched p(CBA-ABOL)/Oligoamines

EDA-terminated hyperbranched polymers were prepared by reaction of the hyperbranched polymers of Tables 1 and 2 with an excess of EDA. The reactions were allowed to proceed until complete disappearance of acryloyl groups had occurred, as was confirmed by NMR.

TABLE 3

|  | Hyperbranched polymer | | | |
|---|---|---|---|---|
|  | p(CBA-ABOL)/ PEI-13% | p(CBA-ABOL)/ PEI-7% | p(CBA-ABOL)/ PEI-4% | p(CBA-ABOL)/ PEI-2% |
| Sample No. | 1 | 2 | 3 | 4 |
| Sample No. of EDA-terminated hyperbranched polymer | 8 | 9 | 10 | 11 |

Example 5

Synthesis of p(CBA-ABOL)/Oligoamine Nanogels (NG-PAAs)

The following hyperbranched polymers (cf. Table 3) were cross-linked as follows.

TABLE 4

|  | Hyperbranched polymer | | | |
|---|---|---|---|---|
|  | p(CBA-ABOL)/ PEI-2% | p(CBA-ABOL)/ PEI-4% | p(CBA-ABOL)/ PAMAM-6% | p(CBA-ABOL)/ PAMAM-4% |
| Sample No. of NG-PAA | 12 | 13 | 14 | 15 |

A solution of 500 mg acryloyl-terminated p(CBA-ABOL)/ oligoamine (oligoamine=PEI or PAMAM) was acidified at room temperature with 4 M HCl to pH~4. The methanol was evaporated from the reaction solution in a flux of nitrogen. The volume of the solution was subsequently adjusted to 4 ml with deionized water. After the addition of 5 mg of photoinitiator Igracure 2959, the water phase was emulsified in 30 ml of mineral oil containing 10% of ABIL EM 90 surfactant through ultrasonication (Bandelin Sonoplus GM 2070) during 5 min (amplitude 75%). Immediately after ultrasonication the nanodroplets were cross-linked by UV irradiation (5 mW/cm$^2$ at 365 nm for 1 h) under stirring. To remove the continuous phase, the emulsion was diluted with 100 ml of acetone/hexane mixture 1/1 (v/v). The cross-linked p(CBA-ABOL)/oligoamine nanogels (with acronym NG-PAAs) were pelleted down by centrifugation (8000 rpm, 5 min), washed from the surfactant four times with acetone/hexane mixture and redispersed in 30 ml deionized water. After purification using a ultrafiltration membrane (MWCO 10000 g/mol) and freeze-drying, the NG-PAAs were stored at −20° C. Yields were 20-25%.

Example 6

Synthesis of Thiol-Functionalized Poly(Ethylene Glycol)s (PEG-SH)

Thiol-functionalized PEG (PEG-SH) with molecular weight of 2000 g/mol was synthesized from methoxy PEG in a three step synthesis as described below.

PEG-Mesylate

The hydroxyl group of methoxy PEG was activated by mesylation according to a slightly modified procedure as was published Elbert et al. (D. L. Elbert, J. A. Hubbell, *Biomacromolecules* 2001, 2, 430). In a typical example 10.0 g (5 mmol, 1 eq) of methoxy PEG ($M_w$=2000 g/mol) was dried twice in an azeotropical distillation of 70 ml of dry toluene. After the second distillation step, the PEG was dissolved in 20 ml of dry dichloromethane followed by the addition of 6.6 ml (15 mmol, 3 eq) of trioctylamine. Subsequently, the solution was cooled down in an ice bath and 1.72 g of mesyl chloride was added dropwisely. The reaction proceeded overnight at room temperature in a nitrogen atmosphere, followed by precipitation in diethyl ether. PEG-mesylate was finally collected as a white powder by filtration and dried under vacuum. Yield: 83%. $^1$H NMR (CDCl$_3$) δ (ppm): 3.08 (s, 3H, OSO$_2$CH$_3$); 3.37 (s, 3H, CH$_3$OCH$_2$); 3.40 (t, 2H, CH$_3$OCH$_2$); 3.52-3.90 (m, 176H, PEG); 4.38 (t, 2H, CH$_2$CH$_2$OSO$_2$CH$_3$).

PEG-Thioacetate

In the second step the mesylate group was converted into a thioacetate according to a modified literature procedure (C. Woghiren, B. Sharma, S. Stein, *Bioconjugate Chem.* 1993, 4, 314). Therefore, 3.0 g (1.5 mmol, 1 eq) of PEG-mesylate was dissolved in 10 ml of dry pyridine and separately 2.23 g (19.5 mmol, 13 eq) of potassium thioacetate was dissolved in 28 ml of a 2/1 (v/v) mixture of dry pyridine/methanol. The PEG-mesylate solution and 2.6 ml of trioctylamine were then added to the potassium thioacetate solution and the reaction mixture was stirred overnight at room temperature in a nitrogen atmosphere. All solvents were evaporated; the residue was dissolved in 10 ml of brine and extracted four times with dichloromethane. The organic phase was dried of magnesium sulfate, concentrated and precipitated twice in diethyl ether. PEG-thioacetate was finally collected as a white powder by filtration and dried under vacuum. Yield: 78%. $^1$H NMR (CDCl$_3$) δ (ppm): 2.33 (s, 3H, CH$_2$SCOCH$_3$); 3.08 (t, 3H, CH$_2$SCOCH$_3$); 3.37 (s, 3H, CH$_3$OCH$_2$); 3.40 (t, 2H, CH$_3$OCH$_2$); 3.52-3.90 (m, 176H, PEG).

PEG-Thiol (PEG-SH)

In the last step the thioacetate was deprotected to yield PEG-SH (O. B. Wallace, D. M. Springer, *Tetrahedron Lett.* 1998, 39, 2693). Therefore, 2.3 g (1.2 mmol, 1 eq) of PEG-thioacetate was dissolved in 10 ml methanol under a nitrogen atmosphere. To this solution 81 mg (1.2 mmol, 1 eq) of sodium thiomethoxide dissolved in 1 ml of methanol was added and the solution was stirred for 30 minutes at room temperature. Then the reaction mixture was poured into 20 ml of 0.1 M aqueous hydrochloric acid and extracted with dichloromethane. The organic layer was washed with brine and all solvents were removed by rotational evaporation. To remove the last impurities, PEG was dissolved in 40 ml demineralized water containing 0.35 g DTT (2.3 mmol, 2 eq) to reduce possibly oxidized thiols and dialyzed by ultrafiltration with a molecular weight cutoff of 1000 g/mol. PEG-SH was finally obtained as a white fluffy powder by lyophilization. Yield: 85%. $^1$H NMR (CDCl$_3$) δ (ppm): 1.59 (t, 1H, CH$_2$CH$_2$SH); 2.68 (q, 2H, CH$_2$CH$_2$SH); 3.37 (s, 3H, CH$_3$OCH$_2$); 3.40 (t, 2H, CH$_3$OCH$_2$); 3.52-3.90 (m, 176H, PEG).

The total conversion from hydroxyl to thiol was determined by Ellman's reagent and proved to be 100%.

Example 7

Preparation of siRNA/Hyperbranched p(CBA-ABOL)/Oligoamine Polyplexes

Polyplexes were prepared from CBA-ABOL (reference; Example 1), sample numbers 1-4 (cf. Table 1) and 5 and 6 (cf. Table 2).

In typical experiment, a solution of siRNA was prepared at a final concentration of 0.025 mg/ml in HEPES buffered glucose (HBG) (pH 7.4). A stock solution of hyperbranched p(CBA-ABOL)/oligoamine (1.25 mg/ml) in HBG (pH 7.4) was prepared and was used for the preparation of polyplexes at 50/1 w/w polymer/siRNA ratio. This solution was repeatedly diluted 1:1 with HBG to prepare polyplexes with 25/1, 12/1 and 6/1 w/w polymer/siRNA ratio. Typically equal volumes of siRNA and hyperbranched p(CBA-ABOL)/oligoamine p(CBA-ABOL)/oligoamine solutions were mixed in a 1 ml Eppendorf tube. After mixing, the polyplex solution was incubated for 20 min at ambient temperature. For higher ratios (or applied dose) increased concentrations of the components were applied.

Example 8 siRNA Loading of NG-PAA Nanogels

The nanogels of Example 4 as well as a nanogel prepared from the diacryloyl macromer (A-(CBA-ABOL)$_n$-A) of Example 1 were loaded with siRNA.

In typical experiment, a solution of siRNA was prepared at a final concentration of 0.025 mg/ml in HEPES buffered glucose (HBG) (pH 7.4). A dispersion of NG-PAAs (1.25 mg/ml) in HBG (pH 7.4) was prepared and was used for loading at 50/1 nanogel/siRNA weight ratio. The NG-PAA dispersion was repeatedly diluted 1:1 with HBG to prepare siRNA loaded nanogels with 25/1, 12/1 and 6/1 polymer/siRNA weight ratio. Typically equal volumes of siRNA and nanogel solutions were mixed in a 1 ml Eppendorf tube and incubated for 20 min at ambient temperature. For higher ratios (or applied doses) higher concentrations of the appropriate components were applied in the same volumes as given above.

Example 9

Ethidium Bromide (EtBr) Displacement Assay

The ability of the EDA-terminated hyperbranched polymers of Example 4 and the NG-PAA nanogels of Example 5 to condense siRNA was studied using an ethidium bromide (EtBr) assay. The p(CBA-ABOL) polymer (Example 1) was used as a reference.

A solution of the hyperbranched polymer or the NG-PAA nanogel was added stepwise to siRNA solution (10 µg/mL) in HBG containing EtBr (0.4 µg/mL). After each step, fluorescence intensity was monitored ($\lambda_{ex}$=510 nm, $\lambda_{em}$=590 nm). The fluorescence intensity of the EtBr solution in the presence of free siRNA corresponded to 0% condensation, whereas the fluorescence intensity without siRNA corresponded to 100% DNA condensation.

Figure 1:
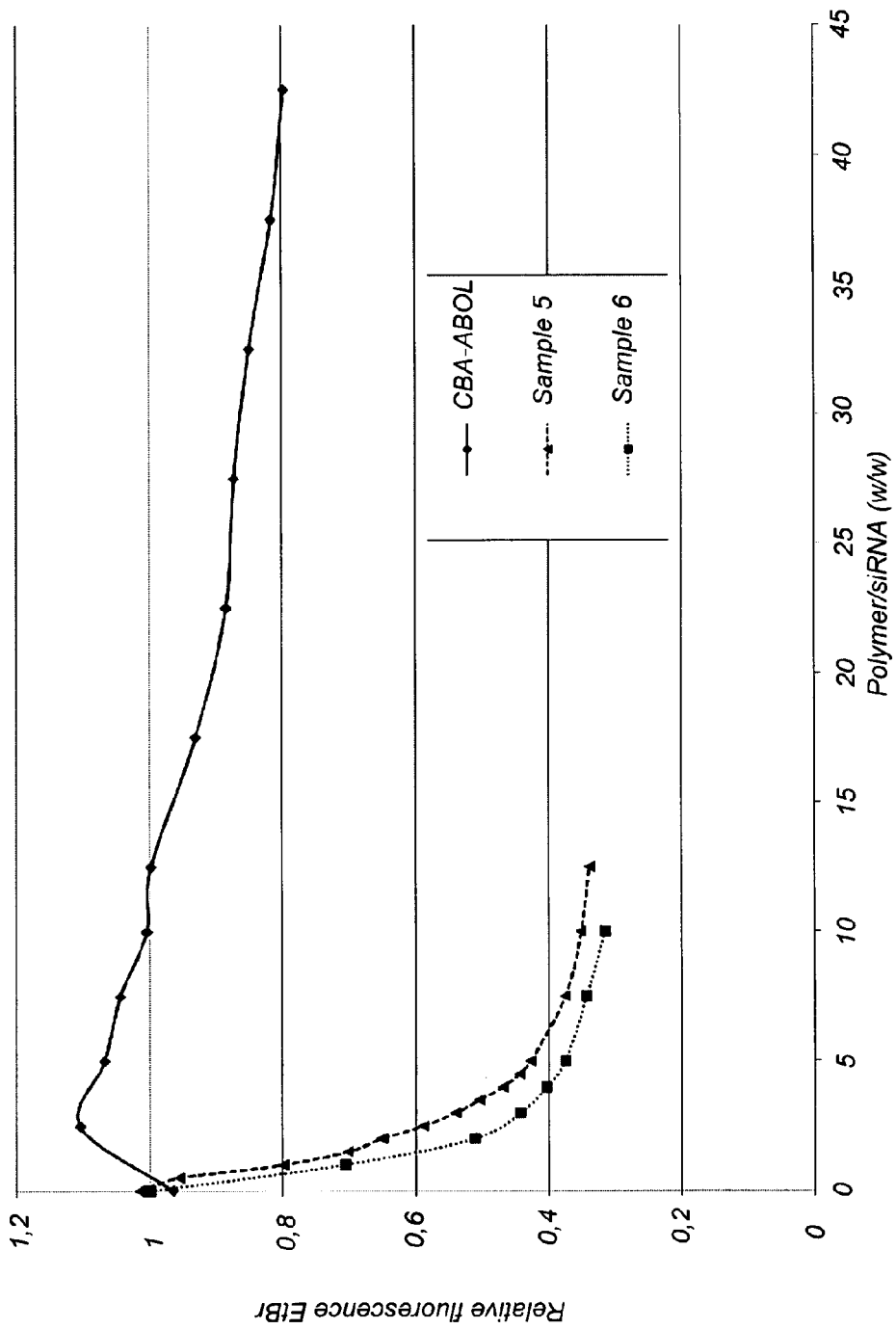
FIG. 1 shows the ability of PA polymers to bind siRNA as established in an EtBr (ethidium bromide) assay. A low fluorescence signal is indicative for efficient shielding (protection) of siRNA.
Figure 2:
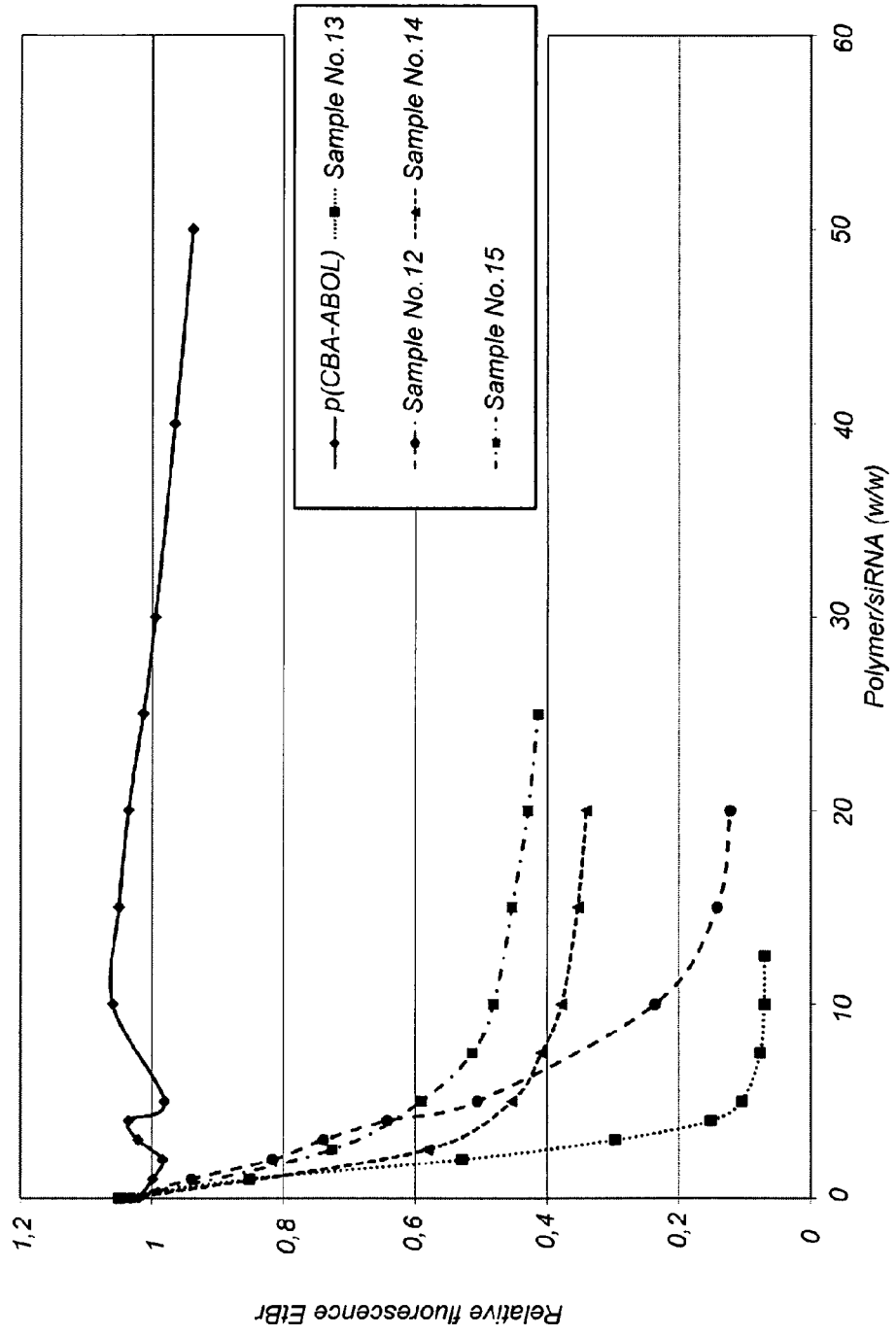
FIG. 2 shows the ability of nanogels comprising a PA polymer to bind and shield siRNA as established in an EtBr (ethidium bromide) assay.
Figure 3:
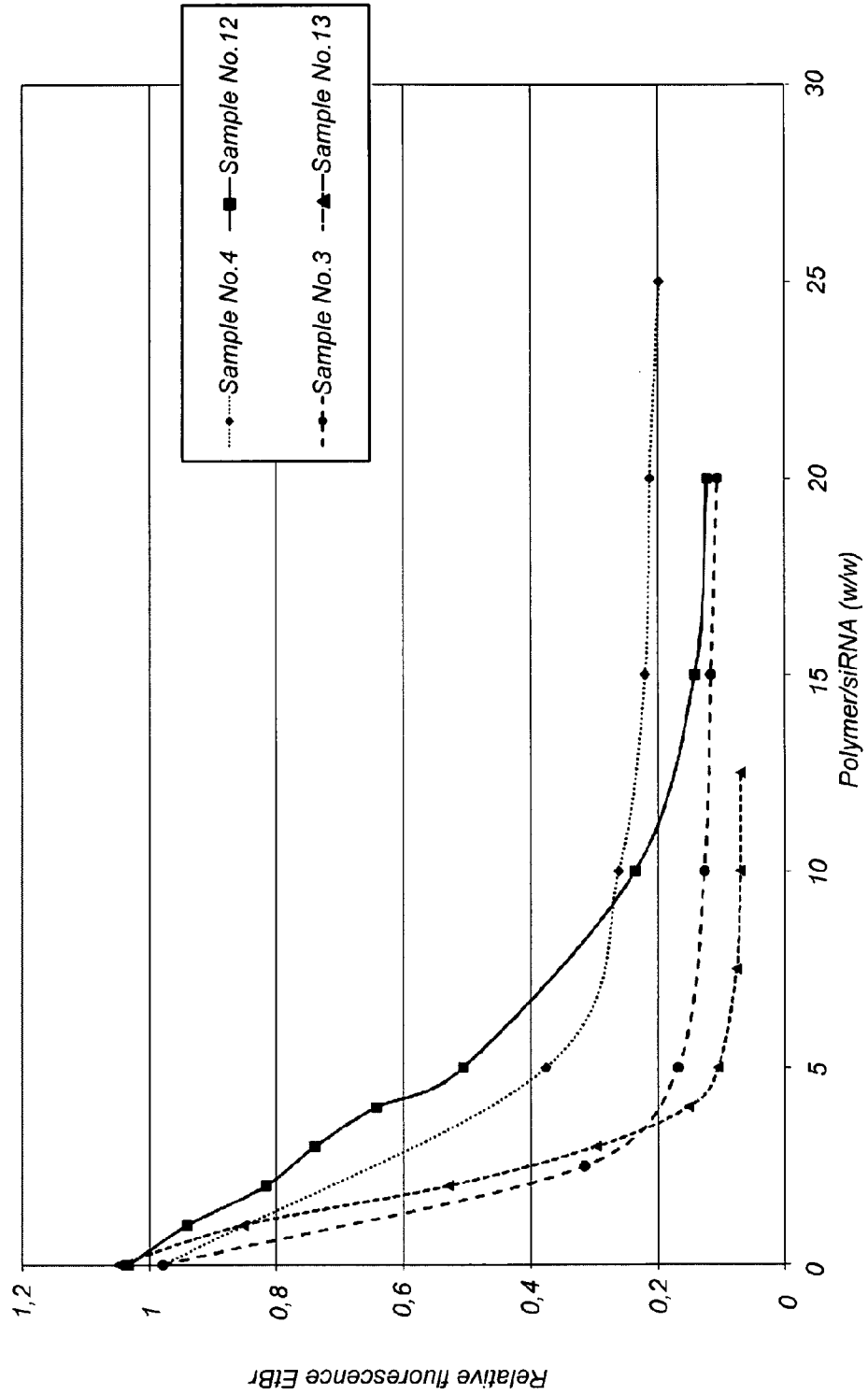
FIG. 3 shows that the nanogels have a higher ability to bind and shield siRNA than the PA polymers (compare Sample Nos. 12 vs. 4, and 13 vs. 3 at higher polymer/siRNA ratio's).

The results are shown in FIGS. 1-3. FIG. 1 shows that the p(CBA-ABOL) polymer itself has a rather low efficiency in siRNA complexation. However, the EDA-terminated hyperbranched polymers and NG-PAA nanogels have a significantly higher binding capacity. EDA-terminated hyperbranched polymers and NG-PAA nanogels containing PEI showed higher affinity to siRNA than those containing PAMAM (FIGS. 1 and 2). The NG-PAA nanogels have a higher ability to condense siRNA than the corresponding EDA-terminated hyperbranched polymers (FIG. 3).

Example 10

In Vitro Gene Silencing

Knockdown efficiency was determined by silencing luciferase expression in NCI-H1299 cells, stably expressing firefly luciferase (donated by prof. G. Storm, University of Utrecht, The Netherlands). Knockdown and cell viability were evaluated in two parallel sessions, using anti-luciferase and non coding siRNA, respectively. Cells were seeded in 96 well plates with a density of 8000 cells per well. After 24 h incubation at 37° C. in a humidified atmosphere containing 5% $CO_2$, medium was replaced with 100 µl fresh serum-free medium. Both anti-luciferase siRNA as non coding siRNA were used. Lipofectamine 2000 (LF) was used as a reference and complexes were prepared according to the manufacturer's protocol. Polyplexes or siRNA loaded nanogels (10 µl per well) were added to the cells in triplo after one hour incubation with fresh medium, resulting in a final siRNA concentration of 72 nM. After two hours of transfection in serumfree medium, polyplex medium was replaced by complete culture medium and the cells were incubated for another 48 h. Cells were lysed in 50 µl lysis buffer and 20 µl of the cell lysate was mixed with 50 µl luciferase assay reagent containing the substrate luciferin. After 100-220 seconds (in this timeframe the emitted light is constant) the luciferase activity was determined by measuring the luminescence at 25° C. for 4 seconds on a PerkinElmer 1420 Victor$^3$ plate reader. Luciferase activity of untreated cells was defined as 100% expression.

FIGS. 4-6 show the gene silencing efficiency of Sample Numbers 1-4 according to Example 2 (FIG. 4), of Sample Numbers 5 and 6 accordfing to Example 3 (FIG. 5) and of the NG-PAA nanogels according to Example 5 (FIG. 6). The numbers on the x-axis represent the polymer/siRNA ratio. The CBA/ABOL polymer did not show any efficiency in siRNA delivery.

Example 11

Measurement of Particle Size and Zeta-Potential

Particle sizes and zeta potentials of loaded and unloaded polyplexes and nanogels were measured by laser-light scattering using a Zetasizer Nano ZS (Malvern, UK).

At high polymer/siRNA mixing ratios (w/w 12 or more) no significant differences in size of the polyplex particles formed by different EDA-terminated hyperbranched polymers were observed. All EDA-terminated hyperbranched polymers formed small polyplexes with sizes ranged from about 80 to about 120 nm and the zeta potentials were about 30 to about 35 mV. At low mixing ratios (i.e. w/w 6) the polyplexes underwent slow aggregation reaching the sizes of about 500 to about 600 nm after mixing for 20 minutes.

The loading of nanogels led to deswelling and gradual decrease of their sizes upon decrease of a mixing ratio. The size of sample no. 12 decreased from about 120 nm (unloaded) to about 90 nm (loaded w/w 50) to about 75 nm (loaded w/w 12).

Further decrease of mixing ratio (increase of siRNA loading) led to aggreagation of the nanogel particles similar to that was observed for the EDA-terminated hyperbranched polymers. The zeta-potentials of the nanogels slightly decreased upon loading. For sample no. 12, the zeta-potential decreased from about 28 mV (unloaded) to about 26 mV (loaded w/w 50) to about 20 mV (loaded w/w 12).

Example 12

Cytotoxicity

Cell viability studies were performed with NCI-H1299 cells in the absence and the presence of 10% FBS. Cells were seeded in 96 well plates with a density of 8000 cells per well 24 h prior to transfection. A dilution series of hyperbranched polymers or NG-PAA nanogel solutions were prepared from 12.5 to 0.02 mg/ml and 10 µl of the solution was added to 100 µl of growth medium. After 24 hours of incubation the cell viability was measured using an XTT assay, in which the XTT value for untreated cells (cells not exposed to transfection systems) was taken as 100% cell viability. Cell viability curves for Sample numbers 4 and 12 in absence of serum are shown in FIG. 7. It is shown that especially the nanogels display the lowest cytotoxicity. For comparison: polymer concentration is 0.055 mg/mL in cell tranfections at polymer/siRNA ratio 48/1.

Example 13

In Vitro Transfection Under Serum Conditions

Transfection studies were performed with NCI-H1299 cells according to a similar procedure as described in Example 10. However, in this case the transfection medium also contained 10% FBS and cells were incubated with siRNA-loaded nanogels during 48 h before the luciferase assay was performed. Sample solutions of siRNA loaded nanogel Sample no. 12 with increasing doses of siRNA (resulting in 125, 250, and 500 ng siRNA per well (100 µL) in the incubation medium, i.e. 72, 144, and 288 nM, respectively), or solutions with constant dosis of siRNA (72 nM) with increasing ratio of nanogel Sample no. 12 were prepared according to the procedure described in Example 8. The luciferase gene silencing results for these different formulations are shown in FIGS. 8 and 9, respectively.

Example 14

Surface Modification of NG-PAA Nanogel Formulations

The surface of sample no. 12 was modified by PEG using an exchange reaction between terminal —SH on the PEG chains and —S—S— groups in the nanogels. In typical experiment the solution of siRNA (0.05 mg/ml) was mixed with an equal volume of nanogel solution of 2.5 mg/ml in HBG (pH 7.4). After mixing the nanogel solution was incubated for 20 min at ambient temperature and an equal volume of the solution of PEG-SH in HBG was added. The concentration of PEG-SH varied from 0.125 mg/ml to 2.5 mg/ml in order to achieve the PEG-SH/nanogel ratios from 0.1 to 2. The sizes and zeta potentials of the nanoparticles were subsequently followed by DLS. For studies of colloid stabilities a defined volume of the solution of NaCl (3.15 M) was added 40 min after addition of PEG-SH in order to achieve final concentration of NaCl 150 mM. After this the sizes of the particles were monitored as a function of time. Results for size and zeta potential are shown in Table 4 before and after surface modification by PEG 2 kDa.

TABLE 5

| | 10% w/w PEG | | 20% w/w PEG | | 40% w/w PEG | | 100% w/w PEG | |
|---|---|---|---|---|---|---|---|---|
| | 0 min | 40 min | 0 min | 40 min | 0 min | 40 min | 0 min | 40 min |
| Size, nm | 91 | 106 | 95 | 109 | 92 | 112 | 94 | 106 |
| Zeta, mV | 26 | 21 | 26 | 21 | 26 | 10.6 | 27 | 8.9 |

FIG. 10 shows data for siRNA delivery to H1299 cells by Sample no. 12 modified with PEG. Polymer/siRNA ratio 50 w/w. Serum free conditions.

Example 15

Stability of Nanogel Formulations Against Freeze-Thaw Cycles and Freeze-Drying

The properties formulations with siRNA of hyperbranched Sample No. 4 and nanogel Sample No. 12 after freeze-thaw cycles and freeze-drying were studied by DLS.

Freezing of Sample No. 4 formulations resulted in aggregation of polyplex nanoparticles. The size of the polyplexes at 50 w/w mixing ratio rose from about 80 nm to about 600 nm after one freeze-taw cycle. It was also not possible to reconstruct the freeze-dried formulation by addition of MilliQ water. After 15 min of vortexing a significant amount of insoluble material was still present in the solution.

In the case of nanogel formulations of Sample No. 12, however, practically no change in size of the particles was observed after both freeze-thawing and freeze-drying. The sizes of the particles at 50 w/w mixing ratio of the initial formulation and those after a freeze-thawing cycle and after a freeze-drying were about 91, about 94 and about 103 nm respectively. The formulations did not lose their activity after these processes (FIG. 11: the grey bars on the left-hand side represent the formulation with anti-LUC siRNA, the grey bar on the right hand side is for non-sense siRNA as a control. Polymer/siRNA ratio 50 w/w. Serum free conditions). All three formulations showed equal efficiency in the knock down of the target gene.

The invention claimed is:

1. A PA polymer according to Formula (1) or (2):

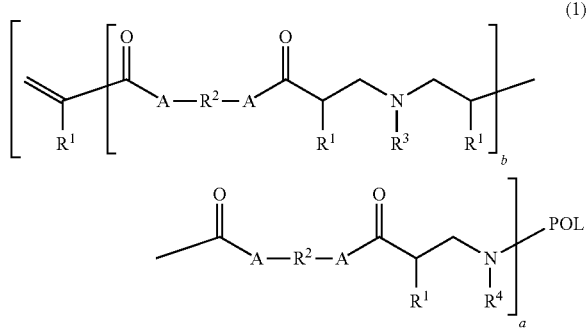

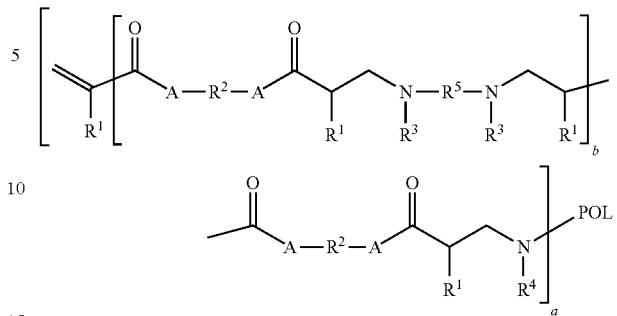

wherein: A is independently selected from a direct carbon-carbon single bond, O, N($R^1$) and S;
$R^1$ is independently selected from H and $CH_3$;
$R^2$ is independently selected from the group consisting of:
(a) $C_1$-$C_{40}$ alkylene, wherein the alkylene group may be linear or branched and is optionally substituted and/or is optionally unsaturated and/or is optionally interrupted by one or more heteroatoms, wherein the heteroatoms are independently selected from O, N and S, and/or wherein the alkylene group is interrupted by one or more —S—S— groups;
(b) $C_3$-$C_{40}$ cycloalkylene, wherein the cycloalkylene group is optionally substituted and/or is optionally unsaturated and/or optionally comprises one or more heteroatoms in the ring, wherein the heteroatoms are independently selected from O, N and S, and/or wherein the cycloalkylene group is interrupted by one or more —S—S— groups outside the ring;
(c) $C_6$-$C_{40}$ arylene, wherein the arylene group is optionally substituted;
(d) $C_6$-$C_{40}$ heteroarylene, wherein the heteroarylene group comprises one, two or three heteroatoms independently selected from O, N and S and/or wherein the heteroarylene group is optionally substituted;
(e) $C_7$-$C_{40}$ alkylarylene wherein the alkylarylene group is optionally substituted and/or wherein an alkyl part of the alkylarylene group is linear or branched and is optionally unsaturated and/or is optionally interrupted by one or more heteroatoms, wherein the heteroatoms are independently selected from O, N and S, and/or wherein an alkyl part of the alkylarylene group is interrupted by one or more —S—S— groups;
(f) $C_7$-$C_{40}$ alkylheteroarylene, wherein the alkylheteroarylene group comprises one, two or three heteroatoms independently selected from O, N and S and/or wherein the alkylheteroarylene group is optionally substituted, and/or wherein an alkyl part of the alkylheteroarylene group is linear or branched and is optionally unsaturated and/or is optionally interrupted by one or more heteroatoms, wherein the heteroatoms are independently selected from O, N and S, and/or wherein an alkyl part of the alkylheteroarylene group is interrupted by one or more —S—S— groups; and
(g) a group wherein two $C_7$-$C_{40}$ (hetero)arylene groups and/or $C_7$-$C_{40}$ alkyl(hetero)arylene groups are connected to each other by a —S—S— group, wherein the alkyl part of the alkyl(hetero)arylene group is linear or branched and is optionally unsaturated and/or is optionally interrupted by one or more heteroatoms, wherein the heteroatoms are independently selected from O, N and S;
$R^3$ is independently selected from the group consisting of:
(a) H;
(b) $C_1$-$C_{10}$ alkyl, wherein the alkyl group may be linear or branched and is optionally substituted and/or is optionally unsaturated and/or is optionally interrupted by one, two or three heteroatoms, wherein the heteroatoms are independently selected from O, N and S;
(C) $C_3$-$C_{12}$ cycloalkyl, wherein the cycloalkyl group is optionally substituted and/or is optionally unsaturated and/or optionally comprises one, two or three heteroatoms in the ring, wherein the heteroatoms are independently selected from O, N and S;
(d) $C_6$-$C_{12}$ aryl, wherein the aryl group is optionally substituted;
(e) $C_6$-$C_{12}$ heteroaryl, wherein the heteroaryl group comprises one, two or three heteroatoms, wherein the heteroatoms are independently selected from O, N and S, and wherein the heteroaryl group is optionally substituted;
(f) $C_7$-$C_{14}$ alkylaryl wherein the alkylaryl group is optionally substituted and/or wherein an alkyl part of the alkylarylene group is linear or branched and is optionally unsaturated and/or is optionally interrupted by one, two or three heteroatoms, wherein the heteroatoms are independently selected from O, N and S; and
(g) $C_7$-$C_{14}$ alkylheteroaryl, wherein the alkylheteroaryl group comprises one, two or three heteroatoms independently selected from O, N and S and/or wherein the alkylheteroarylene group is optionally substituted, and/or wherein an alkyl part of the alkylheteroarylene group is linear or branched and is optionally unsaturated and/or is optionally interrupted by one, two or three heteroatoms, wherein the heteroatoms are independently selected from O, N and S;
$R^4$ is independently selected from the group consisting of:
(a) H;
(b) $C_1$-$C_{10}$ alkyl, wherein the alkyl group may be linear or branched;
(C) $C_3$-$C_{12}$ cycloalkyl;
(d) $C_6$-$C_{14}$ aryl;
(e) $C_6$-$C_{14}$ heteroaryl, wherein the alkylheteroaryl group comprises one, two or three heteroatoms independently selected from O, N and S;
(f) $C_7$-$C_{14}$ alkylaryl; and
(g) $C_7$-$C_{14}$ alkylheteroaryl, wherein the alkylheteroaryl group comprises one, two or three heteroatoms independently selected from O, N and S;
$R^5$ is independently selected from the group consisting of:
(a) $C_1$-$C_{12}$ alkylene, wherein the alkylene group may be linear or branched and is optionally substituted and/or is optionally unsaturated and/or is optionally interrupted by one or more heteroatoms, wherein the heteroatoms are independently selected from O, N and S:
(b) $C_3$-$C_{12}$ cycloalkylene, wherein the cycloalkylene group is optionally substituted and/or is optionally unsaturated and/or optionally comprises one or more heteroatoms in the ring, wherein the heteroatoms are independently selected from O, N and S;
(c) $C_6$-$C_{12}$ arylene, wherein the arylene group is optionally substituted;
(d) $C_6$-$C_{12}$ heteroarylene, wherein the heteroarylene group comprises one, two or three heteroatoms independently selected from O, N and S and/or wherein the heteroarylene group is optionally substituted;
(e) $C_7$-$C_{12}$ alkylarylene wherein the alkylarylene group is optionally substituted and/or wherein an alkyl part of the alkylarylene group is linear or branched and is optionally unsaturated and/or is optionally interrupted by one or more heteroatoms, wherein the heteroatoms are independently selected from O, N and S; and (f) $C_7$-$C_{12}$ alkylheteroarylene, wherein the alkylheteroarylene group comprises one, two or three heteroatoms independently selected from O, N and S and/or wherein the alkylheteroarylene group is optionally substituted, and/or wherein an alkyl part of the alkylheteroarylene group is linear or branched and is optionally unsaturated and/or is optionally interrupted by one or more heteroatoms, wherein the heteroatoms are independently selected from O, N and S;

POL represents a polymeric core having a weight average molecular weight $M_w$ of about 300 to about 25000;

a=2-64; and b=1-50.

2. The polymer according to claim 1, wherein the weight average molecular weight $M_w$ of the polymer core POL is about 300 to about 5000.

3. The polymer according to claim 1, wherein the polymeric core POL is based on or is selected from a branched, hyperbranched, multi-arm, dentritic or star-type (co)polymer.

4. The polymer according to claim 3, wherein the (co)polymer has 2-64 terminal amino groups.

5. The polymer according to claim 4, wherein the amino groups are primary amino groups.

6. The polymer according to claim 1, wherein the polymer core POL is based on or is selected from the group consisting of PEI, PAMAM, PPI, PEAN and PEAC.

7. The polymer according to claim 6, wherein the PEI is represented by the general Formula (5a) or (5b):

(5a)

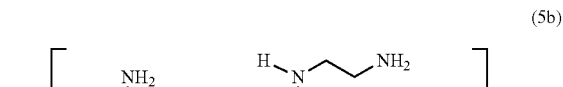
(5b)

wherein n is such that the PEI has a weight average molecular weight $M_w$ of about 600 to about 3000.

8. The polymer according to claim 6, wherein the polymer core POL is based on or is selected from the group consisting of the polymers represented by the general Formulas (6)-(9):

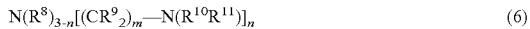
(6)

(7)

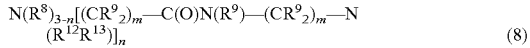
(8)

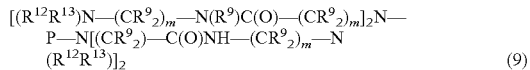
(9)

wherein:

$R^8$ is a hydrogen atom, a linear or branched $C_1$-$C_{20}$ alkyl group or a —[($CR^{14}_2$)$_q$—X]$_o$—$R^{15}$ group, wherein X is O or $N(R^8)$;

m is 2, 3 or 4;

n is 2 or 3;

o is 1-10;

q is 2, 3 or 4;

P is —($CR^9_2$)$_m$—, a $C_6$-$C_{12}$ arylene group, a $C_6$-$C_{12}$ cycloalkylene group or a [($CR^{14}_2$)$_q$—X]$_p$—$C(R^{14})_2$]— group, wherein X is O or $N(R^8)$ and p is 1-10;

$R^9$ is a hydrogen atom or a linear or branched $C_1$-$C_6$ alkyl group;

$R^{10}$ and $R^{11}$ are independently a hydrogen atom, a linear or branched $C_1$-$C_6$ alkyl group or a group of the formula —($CR^{14}_2$)$_q$$NR^{16}R^{17}$, provided that $R^{10}$ and $R^{11}$ are not both a linear or branched $C_1$-$C_6$ alkyl group;

$R^{16}$ and $R^{17}$ are independently a hydrogen atom, a linear or branched $C_1$-$C_6$ alkyl group or a group of the formula —($CR^{14}_2$)$_q$$NR^{18}R^{19}$, provided that $R^{16}$ and $R^{17}$ are not both a linear or branched $C_1$-$C_6$ alkyl group;

$R^{18}$ and $R^{19}$ are independently a hydrogen atom, a linear or branched $C_1$-$C_6$ alkyl group or a group of the formula —($CR^{14}_2$)$_q$$NR^{20}R^{21}$, provided that $R^{18}$ and $R^{19}$ are not both a linear or branched $C_1$-$C_6$ alkyl group;

$R^{20}$ and $R^{21}$ are independently a hydrogen atom or a linear or branched $C_1$-$C_6$ alkyl group, provided that $R^{20}$ and $R^{21}$ are not both a linear or branched $C_1$-$C_6$ alkyl group;

$R^{22}$ is a hydrogen atom or a methyl group, provided that at least one $R^{22}$ is a hydrogen atom;

$R^{15}$ is a hydrogen or linear or branched $C_1$-$C_{20}$ alkyl group;

$R^{12}$ and $R^{13}$ are independently a hydrogen atom, a linear or branched $C_1$-$C_6$ alkyl group or a group of the formula —($CR^9_2$)$_m$—C(O)NH—($CR^9_2$)$_m$—$N(R^{23}R^{24})$, provided that $R^{12}$ and $R^{13}$ are not both a linear or branched $C_1$-$C_6$ alkyl group;

$R^{23}$ and $R^{24}$ are independently a hydrogen atom, a linear or branched $C_1$-$C_6$ alkyl group or a group of the formula —($CR^9_2$)$_m$—C(O)NH—($CR^9_2$)$_m$—$N(R^{25}R^{26})$, provided that $R^{23}$ and $R^{24}$ are not both a linear or branched $C_1$-$C_6$ alkyl group;

$R^{25}$ and $R^{26}$ are independently a hydrogen atom, a linear or branched $C_1$-$C_6$ alkyl group or a group of the formula —($CR^9_2$)$_m$—C(O)NH—($CR^9_2$)$_m$—$N(R^{27}R^{28})$, provided that $R^{25}$ and $R^{26}$ are not both a linear or branched $C_1$-$C_6$ alkyl group; and $R^{27}$ and $R^{28}$ are independently a hydrogen atom or a linear or branched $C_1$-$C_6$ alkyl group, provided that $R^{27}$ and $R^{28}$ are not both a linear or branched $C_1$-$C_6$ alkyl group.

9. A process for the preparation of a PA polymer of claim 1 according to general Formulas (1) or (2), said process comprising the steps of:

(1) reacting a monomer (I) according to general formula (12):

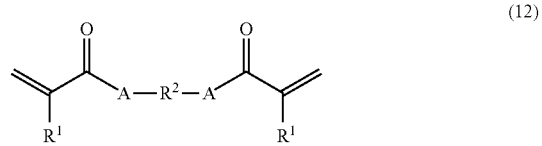

(12)

wherein $R^1$, A, and $R^2$ are as defined in claim 1, with a monomer (II) according to general Formula (13) or a monomer (III) according to general Formula (14):

$(H_2N)$—$R^3$                            (13)

$HR^3N$—$R^5$—$NR^3H$                  (14)

wherein $R^3$ and $R^5$ are as defined in claim 1, in a molar ratio of monomer (I):monomer (II) of from about 1.5:1 to about 10:1 to form a macromer according to general Formula (15) or (16):

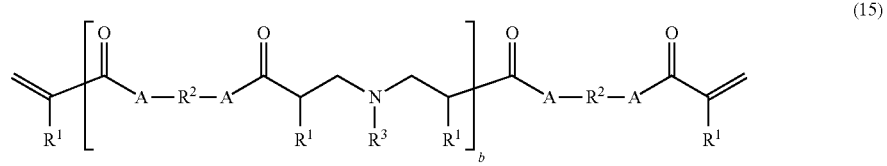

(15)

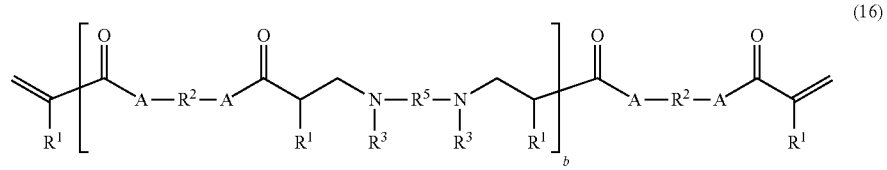

(16)

wherein b is as defined in claim 1; and (2) reacting the macromer according to general Formula (15) or (16) with a polymer according to Formula (17):

      (17)

wherein a and $R^4$ are as defined in claim 1 and wherein at least one $R^4$ is H.

10. A PA polymer according to general Formulas (1) or (2) obtainable by the process according to claim 9.

11. A nanogel comprising the PA polymer according to claim 1.

12. The nanogel according to claim 11, wherein the nanogel comprises a biologically active component.

13. The nanogel according to claim 12, wherein the biologically active component is selected from the group consisting of RNA (in particular siRNA and miRNA) or derivatives or fragments hereof, DNA or derivatives or fragments hereof, (oligo)peptides and derivatives thereof, and proteins and derivatives thereof.

14. A process for preparing a nanogel comprising cross-linking a PA polymer according to general Formulas (1) or (2) according to claim 1.

15. The process according to claim 14, wherein the cross-linking is conducted by UV radiation.

16. A nanoparticle having the general Formula (3) or (4):

(a") H;

(b") $C_1$-$C_{10}$ alkyl, wherein the alkyl group may be linear or branched and is optionally substituted and/or is optionally unsaturated and/or is optionally interrupted by one, two or three heteroatoms, wherein the heteroatoms are independently selected from O, N and S;

(c") $C_3$-$C_{12}$ cycloalkyl, wherein the cycloalkyl group is optionally substituted and/or is optionally unsaturated and/or optionally comprises one, two or three heteroatoms in the ring, wherein the heteroatoms are independently selected from O, N and S;

(d") $C_6$-$C_{12}$ aryl, wherein the aryl group is optionally substituted;

(e") $C_6$-$C_{12}$ heteroaryl, wherein the heteroaryl group comprises one, two or three heteroatoms independently selected from O, N and S and/or wherein the heteroaryl group is optionally substituted;

(f") $C_7$-$C_{14}$ alkylaryl wherein the alkylaryl group is optionally substituted and/or wherein an alkyl part of the alkylarylene group is linear or branched and is optionally unsaturated and/or is optionally interrupted by one, two or three heteroatoms, wherein the heteroatoms are independently selected from O, N and S; and (g") $C_7$-$C_{14}$ alkylheteroaryl, wherein the alkylheteroaryl group comprises one, two or three heteroatoms indepen-

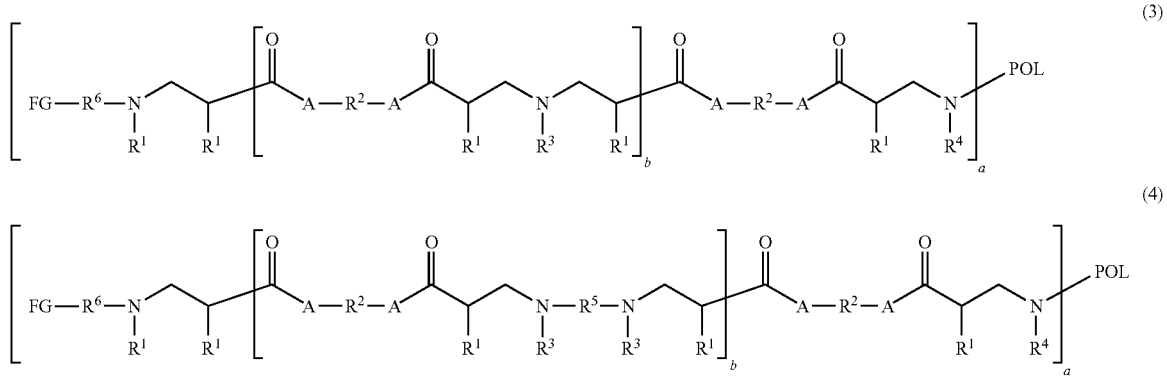

wherein $R^1$, $R^2$, $R^3$, $R^4$, $R^5$, A, POL, a and b are as defined in claim 1; and $R^6$ is selected from the group consisting of:

(a) $C_1$-$C_{40}$ alkylene, wherein the alkylene group may be linear or branched and is optionally substituted and/or is optionally unsaturated and/or is optionally interrupted by one or more heteroatoms, wherein the heteroatoms are independently selected from O, N and S, and/or wherein the alkylene group is interrupted by one or more —S—S— groups; or (b) $C_3$-$C_{40}$ cycloalkylene, wherein the cycloalkylene group is optionally substituted and/or is optionally unsaturated and/or optionally comprises one or more heteroatoms in the ring, wherein the heteroatoms are independently selected from O, N and S, and/or wherein the cycloalkylene group is interrupted by one or more —S—S— groups outside the ring; and FG is a Functional Group which is selected from the group consisting of —OH, —$OR^7$, —$NH_2$, —$NH(R^7)$, —$N(R^7)_2$, —$C(O)OR^7$, —$C(O)R^7$, —$C(O)NHR^7$, and —$C(O)NR^7_2$, wherein $R^7$ is independently selected from the group consisting of:

dently selected from O, N and S and/or wherein the alkylheteroarylene group is optionally substituted, and/or wherein an alkyl part of the alkylheteroarylene group is linear or branched and is optionally unsaturated and/or is optionally interrupted by one, two or three heteroatoms, wherein the heteroatoms are independently selected from O, N and S.

17. A process for preparing a nanoparticle comprising reacting a PA polymer according to general Formulas (1) or (2) according to claim 1 with a reagent according to formulas (26a) or (26b):

      (26a)

      (26b)

wherein $R^6$ is selected from the group consisting of:

(a) $C_1$-$C_{40}$ alkylene, wherein the alkylene group may be linear or branched and is optionally substituted and/or is optionally unsaturated and/or is optionally interrupted by one or more heteroatoms, wherein the heteroatoms are independently selected from O, N and S, and/or wherein the alkylene group is interrupted by one or more —S—S— groups; or (b) $C_3$-$C_{40}$ cycloalkylene wherein the cycloalkylene group is optionally substituted and/or is optionally unsaturated and/or optionally comprises one or more heteroatoms in the ring, wherein the heteroatoms are independently selected from O, N and S, and/or wherein the cycloalkylene group is interrupted by one or more —S—S— groups outside the ring;

FG is H or a Functional Group which is selected from the group consisting of —OH, —OR$^7$, —NH$_2$; —NH(R$^7$), —NH(R$^7$)2, —C(O)OR$^7$, —C(O)R$^7$, —C(O)NHR$^7$, and —C(O)NR$^7_2$, wherein R$^7$ is independently selected from the group consisting of:

(a") H;
(b") $C_1$-$C_{10}$ alkyl, wherein the alkyl group may be linear or branched and is optionally substituted and/or is optionally unsaturated and/or is optionally interrupted by one, two or three heteroatoms, wherein the heteroatoms are independently selected from O, N and S;
(c") $C_3$-$C_{12}$ cycloalkyl, wherein the cycloalkyl group is optionally substituted and/or is optionally unsaturated and/or optionally comprises one, two or three heteroatoms in the ring, wherein the heteroatoms are independently selected from O, N and S;
(d") $C_6$-$C_{12}$ aryl, wherein the aryl group is optionally substituted;
(e") $C_6$-$C_{12}$ heteroaryl, wherein the heteroaryl group comprises one, two or three heteroatoms independently selected from O, N and S and/or wherein the heteroaryl group is optionally substituted;
(f") $C_7$-$C_{14}$ alkylaryl wherein the alkylaryl group is optionally substituted and/or wherein an alkyl part of the alkylarylene group is linear or branched and is optionally unsaturated and/or is optionally interrupted by one, two or three heteroatoms, wherein the heteroatoms are independently selected from O, N and S; and
(g") $C_7$-$C_{14}$ alkylheteroaryl, wherein the alkylheteroaryl group comprises one, two or three heteroatoms independently selected from O, N and S and/or wherein the alkylheteroarylene group is optionally substituted, and/or wherein an alkyl part of the alkylheteroarylene group is linear or branched and is optionally unsaturated and/or is optionally interrupted by one, two or three heteroatoms, wherein the heteroatoms are independently selected from O, N and S; and R$^{30}$ is independently selected from the group consisting of:
(a) H;
(b) $C_1$-$C_{10}$ alkyl, wherein the alkyl group may be linear or branched and is optionally substituted and/or is optionally unsaturated and/or is optionally interrupted by one, two or three heteroatoms, wherein the heteroatoms are independently selected from O, N and S;
(c) $C_3$-$C_{12}$ cycloalkyl, wherein the cycloalkyl group is optionally substituted and/or is optionally unsaturated and/or optionally comprises one, two or three heteroatoms in the ring, wherein the heteroatoms are independently selected from O, N and S;
(d) $C_6$-$C_{12}$ aryl, wherein the aryl group is optionally substituted;
(e) $C_6$-$C_{12}$ heteroaryl, wherein the heteroaryl group comprises one, two or three heteroatoms independently selected from O, N and S and/or wherein the heteroaryl group is optionally substituted;
(f) $C_7$-$C_{14}$ alkylaryl wherein the alkylaryl group is optionally substituted and/or wherein an alkyl part of the alkylarylene group is linear or branched and is optionally unsaturated and/or is optionally interrupted by one, two or three heteroatoms, wherein the heteroatoms are independently selected from O, N and S; and
(g) $C_7$-$C_{14}$ alkylheteroaryl, wherein the alkylheteroaryl group comprises one, two or three heteroatoms independently selected from O, N and S and/or wherein the alkylheteroarylene group is optionally substituted, and/or wherein an alkyl part of the alkylheteroarylene group is linear or branched and is optionally unsaturated and/or is optionally interrupted by one, two or three heteroatoms, wherein the heteroatoms are independently selected from O, N and S.

18. A surface modified nanogel obtained by a process comprising the steps of:
(1) cross-linking a PA polymer according to general Formulas (1) or (2) according to claim 1;
(2) optionally loading the nanogel with a biologically active component; and
(3) reacting the nanogel with a reactant R-CFG or R'—SH, wherein:
R and R' are selected from the group consisting of 2-thioethyl, 2-hydroxyethyl, PEG (polyethylene oxide) residues and PPO (polypropylene oxide) residues, wherein the PEG residues and the PPO residues have a number average molecular weight $M_n$ of about 500 to about 10000; CFG is a group capable of forming a covalent bond with a group FG, wherein FG is H or a Functional Group which is selected from the croup consisting of —OH, —OR$^7$, —NH$_2$; —NH(R$^7$), —N(R$^7$)$_2$, —C(O)OR$^7$, —C(O)R$^7$, —C(O)NHR$^7$, and —C(O)NR$^7_2$, wherein R$^7$ is independently selected from the group consisting of:
(a") H;
(b") $C_1$-$C_{10}$ alkyl, wherein the alkyl group may be linear or branched and is optionally substituted and/or is optionally unsaturated and/or is optionally interrupted by one, two or three heteroatoms, wherein the heteroatoms are independently selected from O, N and S;
(c") $C_3$-$C_{12}$ cycloalkyl, wherein the cycloalkyl group is optionally substituted and/or is optionally unsaturated and/or optionally comprises one, two or three heteroatoms in the ring, wherein the heteroatoms are independently selected from O, N and S;
(d") $C_6$-$C_{12}$ aryl, wherein the aryl group is optionally substituted;
(e") $C_6$-$C_{12}$ heteroaryl, wherein the heteroaryl group comprises one, two or three heteroatoms independently selected from O, N and S and/or wherein the heteroaryl group is optionally substituted;
(f") $C_7$-$C_{14}$ alkylaryl wherein the alkylaryl group is optionally substituted and/or wherein an alkyl part of the alkylarylene group is linear or branched and is optionally unsaturated and/or is optionally interrupted by one, two or three heteroatoms, wherein the heteroatoms are independently selected from O, N and S; and
(g") $C_7$-$C_{14}$ alkylheteroaryl, wherein the alkylheteroaryl group comprises one, two or three heteroatoms independently selected from O, N and S and/or wherein the alkylheteroarylene group is optionally substituted, and/or wherein an alkyl part of the alkylheteroarylene group is linear or branched and is optionally unsaturated and/or is optionally interrupted by one, two or three heteroatoms, wherein the heteroatoms are independently selected from O, N and S; and
wherein the sequence of steps (1), (2) and (3) is: (1)-(2)-(3), (1)-(3)-(2), or (3)-(1)-(2).

* * * * *